(12) United States Patent
Satta et al.

(10) Patent No.: US 7,522,697 B2
(45) Date of Patent: Apr. 21, 2009

(54) X-RAY CT APPARATUS

(75) Inventors: Yusuke Satta, Tokyo (JP); Kazuhiko Sato, Tokyo (JP); Akihiko Nishide, Tokyo (JP); Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 71 days.

(21) Appl. No.: 11/680,404

(22) Filed: Feb. 28, 2007

(65) Prior Publication Data

US 2008/0031407 A1 Feb. 7, 2008

(30) Foreign Application Priority Data

Mar. 1, 2006 (JP) ............................. 2006-055417

(51) Int. Cl.
*G21K 1/12* (2006.01)
(52) U.S. Cl. ............................. 378/15; 378/19; 378/20
(58) Field of Classification Search ............ 378/4, 378/15, 19, 20, 62, 162, 208, 209
See application file for complete search history.

(56) References Cited

U.S. PATENT DOCUMENTS

| | | | |
|---|---|---|---|
| 5,768,336 A | 6/1998 | Khutoryansky et al. | |
| 5,787,886 A | 8/1998 | Kelly et al. | |
| 6,580,777 B1 * | 6/2003 | Ueki et al. | 378/17 |
| 6,816,567 B2 * | 11/2004 | Drummond et al. | 378/16 |
| 6,977,984 B2 | 12/2005 | Hsieh et al. | |
| 7,173,997 B2 | 2/2007 | Hagiwara | |
| 7,426,255 B2 * | 9/2008 | Miyazaki et al. | 378/8 |
| 2003/0161435 A1 * | 8/2003 | Ozaki | 378/4 |

\* cited by examiner

*Primary Examiner*—Irakli Kiknadze
(74) *Attorney, Agent, or Firm*—Armstrong Teasdale LLP

(57) ABSTRACT

The present invention is to easily associate X-ray projection data and scanning table z-direction coordinate information with each other. Using set parameters of the operations of a scanning gantry and a scanning table, the association of the X-ray projection data and scanning table z-direction coordinate information with each other is executed. Thereafter, image reconstruction is carried out based on the X-ray projection data to obtain a tomographic image. The operation set parameters are stored as part of the X-ray projection data. Alternatively, they are collectively stored even in the case of files separate from the X-ray projection data.

14 Claims, 19 Drawing Sheets

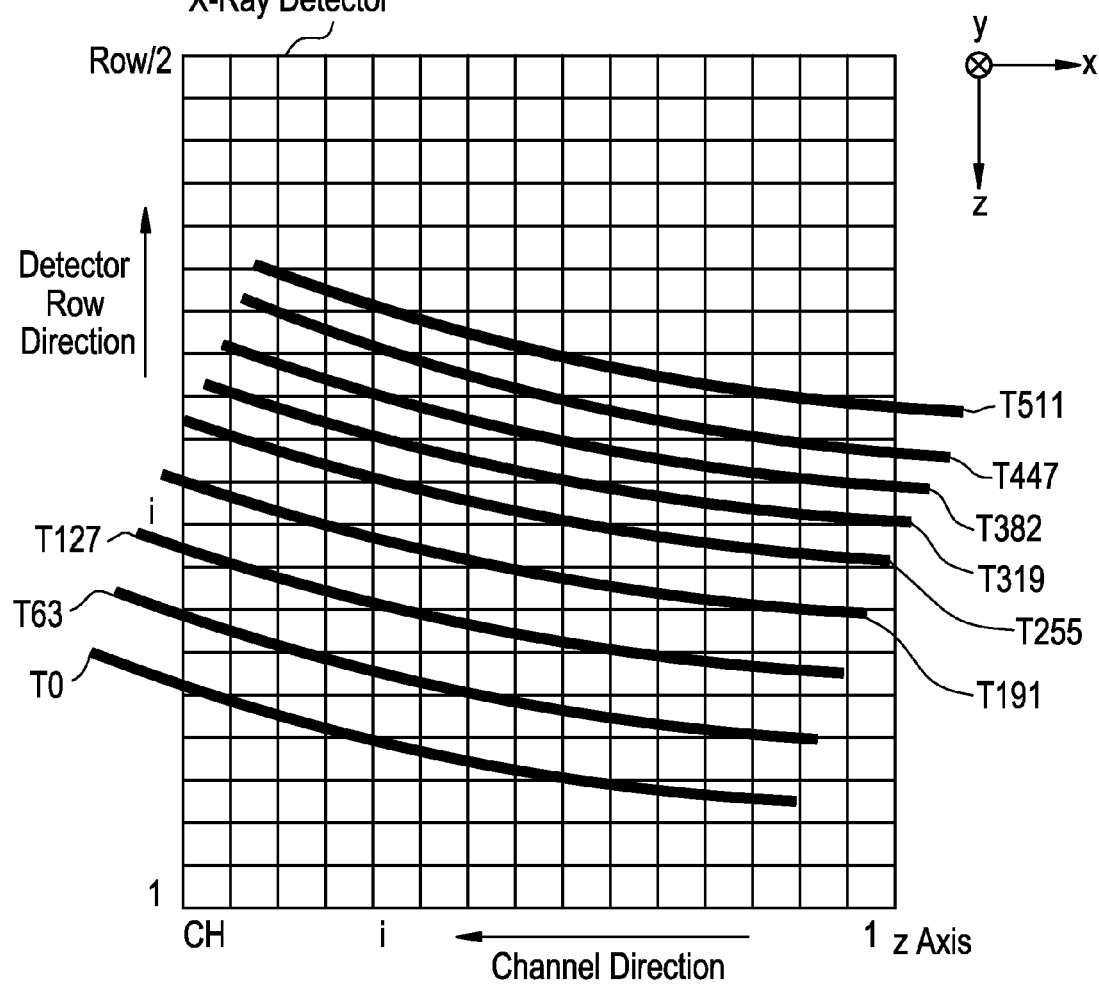

Dr (0°, x, y)

D2 (0°, x, y)

FIG. 16
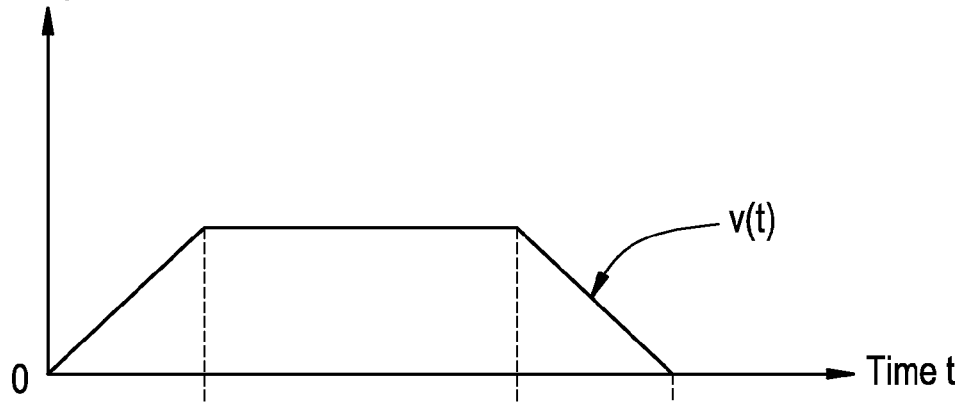
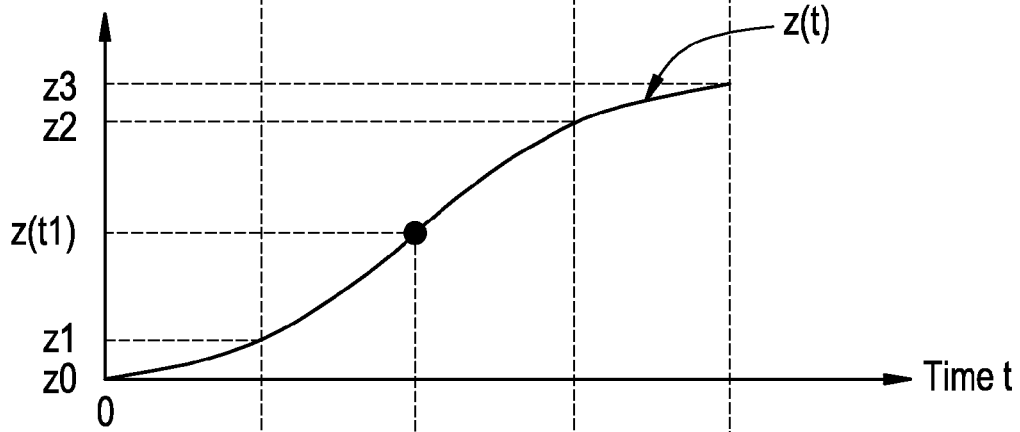
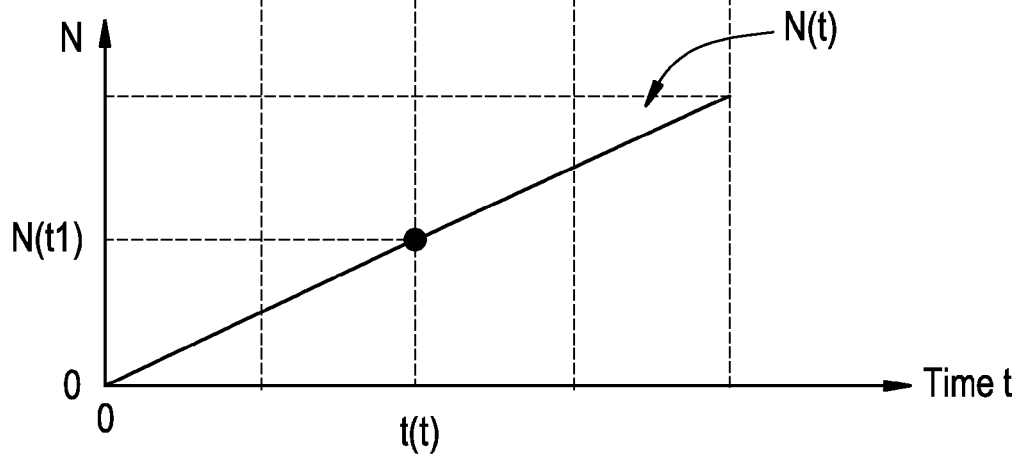

FIG. 19

| z-Direction Coordinates | z0→z3 | z3→z0 | z0→z3 |
|---|---|---|---|
| Scanning Table Initial Position | z0 | z3 | z0 |
| Scanning Table Acceleration End Position | z1 | z2 | z1 |
| Scanning Table Deceleration Start Position | z2 | z1 | z2 |
| Scanning Table Stop Position | z3 | z0 | z3 |
| Scanning Table Acceleration | a1 | a2 | a1 |
| Scanning Table Deceleration | a2 | a1 | a2 |
| Scanning Table Constant Velocity | v1 | -v1 | v1 |

X-RAY CT APPARATUS

CROSS REFERENCE TO RELATED APPLICATIONS

This application claims the benefit of Japanese Application No. 2006-055417 filed Mar. 1, 2006.

BACKGROUND OF THE INVENTION

The present invention relates to an X-ray CT apparatus which is a medical X-ray CT (Computed Tomography) apparatus or an industrial X-ray CT apparatus and which holds operations of an X-ray data acquisition system or information for imaging conditions and performs image reconstruction based on the same, upon a conventional scan (axial scan), a cine scan, a helical scan, a variable-pitch helical scan or a helical shuttle scan.

An X-ray CT apparatus acquires X-ray projection data by scanning a subject with X rays and image-reconstructs a tomographic image of the subject, based on the X-ray projection data (refer to, for example, Japanese Unexamined Patent Publication No. 2004-173756).

Such an X-ray CT apparatus has a two-dimensional X-ray area detector of a matrix structure typified by, for example, a multi-row X-ray detector or a flat panel. Upon data acquisition by a conventional scan (axial scan), a cine scan or a helical scan, a scanning table is changed in a z direction by the operation of an X-ray data acquisition system during scan to perform X-ray data acquisition. In the case of a variable-pitch helical scan and a helical shuttle scan, an absolute coordinate position or a relative coordinate position of a z-direction coordinate of the scanning table is recorded for each view or at several views as position information of the scanning table. Described specifically, when a scanning table velocity changes like $v(t)$ as shown in FIG. 16, a scanning table position changes like $z(t)$ and a data acquisition view number linearly increases like $N(i)$. Therefore, for example, data of a scanning table position $z(t1)$ is recorded so as to correspond to an $N(t1)$ view. Incidentally, the data of the scanning table position $z(t1)$ may be recorded with being added to X-ray projection data.

Here, an encoder for detecting a position is installed in the scanning table as in the case of a rotary encoder, a linear encoder or the like, and the installed encoder is used to obtain data about each position of the scanning table in real time during scan. For example, X-ray projection data and position data of the scanning table at the time that the X-ray projection data is obtained, are stored in association with each other. For example, as file data different from the X-ray projection data, the position data of the scanning table is stored in association with it each other. Thereafter, image reconstruction is carried out using the X-ray projection data and the position data of the scanning table both associated with each other, thereby to obtain a tomographic image of the subject.

Therefore, there is a case in which the addition of the X-ray projection data to each view is not easy. Further, there was a case where when z-direction coordinate information of the scanning table corresponding to each view was contained as another file, it was not easy to associate the z-direction coordinate information of the scanning table and each view for the X-ray projection data with each other upon image reconstruction.

Thus, there was a case in which a problem arose in that the association of the X-ray projection data and the scanning table z-direction coordinate information with each other upon the X-ray projection data acquisition or image reconstruction was not easy.

In an X-ray CT apparatus having a multi-row X-ray detector or an X-ray CT apparatus having a two-dimensional X-ray area detector typified by a flat panel, there is a tendency to increase the number of channels of an X-ray detector and increase the number of views for X-ray projection data as the resolution in a row direction rises. Further, there is a tendency to make the rotational velocity of the gantry fast. That is, the number of views per unit time trends to increase. A z-direction position of a scanning table or cradle is measured by the scanning table. Its z-direction position data is added to X-ray projection data obtained by a data acquisition system (DAS) of a scanning gantry rotating section at a scanning gantry fixing section. Therefore, this control becomes difficult due to the increase in the number of views per unit time.

Thus, an object of the present invention is to provide an X-ray CT apparatus capable of efficiently describing and storing position information and photography information of an X-ray data acquisition system by less parameters.

SUMMARY OF THE INVENTION

When an operator sets an imaging condition, the operations of an X-ray data acquisition system and a scanning table or cradle are determined. The scanning table or cradle will be explained below as the scanning table. That is, as the operations of the X-ray data acquisition system and the scanning table with a subject placed thereon, a scanning table z-direction coordinate position, a scanning table x-direction coordinate position, a scanning table y-direction coordinate position, a scanning gantry rotating section rotation-angle position, a scanning gantry tilt angle position, a scanning gantry x-direction coordinate position, a scanning gantry y-direction coordinate position, and a scanning gantry z-direction coordinate position are predicted upon setting of the imaging condition. Since the X-ray data acquisition system and the scanning table are normally feedback-controlled with an accuracy of 0.1 mm or less, they do not deviate vastly from their predicted values. Therefore, if the predicted operations of X-ray data acquisition system and scanning table can be described by several parameters, then the operations of the X-ray data acquisition system and the scanning table can be reproduced if the parameters are recorded.

FIG. 17 describes the manner of traveling of the scanning table (or cradle) in the z direction. If parameters for cradle acceleration, cradle deceleration, a cradle stationary velocity, a cradle initial position, a cradle stop position, a cradle acceleration end position and a cradle deceleration start position exist, then the operation of the scanning table or cradle can be described.

If the scanning gantry and the scanning table corresponding to the X-ray data acquisition system can be moved with sufficient accuracy as predicted based on the parameters, it is then unnecessary to subject information about a scanning table z-direction coordinate position, a scanning table x-direction coordinate position, a scanning table y-direction coordinate position, a scanning gantry rotating section rotation-angle position, a scanning gantry tilt angle position, a scanning gantry x-direction coordinate position, a scanning gantry y-direction coordinate position, and a scanning gantry z-direction coordinate position set for each view to measurement, data acquisition and addition to X-ray projection data.

Therefore, in the present invention, the operation of a scanning gantry corresponding to an X-ray data acquisition system, and the operation of a scanning table or cradle are predicted when an operator sets an imaging condition, and described with operation parameters. When the parameters are added to X-ray projection data upon X-ray data acquisition to perform image reconstruction, the image reconstruction is carried out using the operation parameters. Alternatively, the operation parameters are inserted into another file and associated with the X-ray projection data. Upon execution of image reconstruction, the image reconstruction is carried out using the operation parameters.

In order to solve the above problems, there is provided an X-ray CT apparatus according to a first aspect, comprising a scanning table for placing a subject thereon and moving the subject placed thereon;

a scanning gantry comprising an X-ray generator, an X-ray detector for detecting the X rays in opposition to the X-ray generator, and a rotation device for rotating the X-ray generator and the X-ray detector, for causing the X-ray generator to expose X rays to the subject moved by the scanning table while the X-ray generator and the X-ray detector are being rotated about the subject, and performing a scan for causing the X-ray detector to detect the X rays transmitted through the subject thereby to acquire X-ray projection data;

image reconstructing device for image-reconstructing the X-ray projection data acquired by the scanning gantry;

image display device for displaying a tomographic image reconstructed by the image reconstructing device; and imaging condition setting device for setting an imaging condition including a parameter for operating the scanning gantry and/or a parameter for causing the scanning table to move the subject upon execution of the scan, wherein the image reconstructing device reconstructs the X-ray projection data using the parameter for operating the scanning gantry and/or the parameter for causing the scanning table to move the subject set by the imaging condition setting device as the imaging condition.

In the X-ray CT apparatus according to the first aspect, the operations of an X-ray data acquisition system comprising the X-ray data acquisition device and the scanning table are recognized in advance by operation parameters. Since the position of an X-ray beam passing through each pixel on an image reconstruction plane can be predicted properly upon image reconstruction, the image reconstruction can be carried out with a high degree of accuracy.

In order to solve the above problems, there is provided an X-ray CT apparatus according to a second aspect, wherein in the X-ray CT apparatus according to the first aspect, the X-ray data acquisition device adds the parameters set as the imaging condition by the imaging condition setting device to the X-ray projection data and records the result of addition therein.

In the X-ray CT apparatus according to the second aspect, the operations of an X-ray data acquisition system comprising the X-ray data acquisition device and scanning table are recognized in advance by operation parameters, and the operation parameters are added to X-ray projection data. Since the position of an X-ray beam passing through each pixel on an image reconstruction plane can be predicted properly based on the operation parameters added to the X-ray projection data upon image reconstruction, the image reconstruction can be performed accurately.

In order to solve the above problems, there is provided an X-ray CT apparatus according to a third aspect, wherein the X-ray data acquisition device records, as parameters for the operations of the X-ray data acquisition device and the scanning table, data containing at least one of a scanning table z-direction coordinate position, a scanning table x-direction coordinate position, a scanning table y-direction coordinate position, a scanning gantry rotating section rotation-angle position, a scanning gantry tilt angle position, a scanning gantry x-direction coordinate position, a scanning gantry y-direction coordinate position, and a scanning gantry z-direction coordinate position.

In the X-ray CT apparatus according to the third aspect, even when the scanning gantry, and the X-ray data acquisition device and scanning table lying thereinside are allowed to perform photography and diagnoses by various applications or various operations, the operations of the X-ray data acquisition system comprising the X-ray data acquisition device and scanning table lying in the scanning gantry are recognized more by respective operation parameters. If the scanning gantry and the X-ray data acquisition device and scanning table lying thereinside can be moved with satisfactory accuracy as recognized, then an X-ray beam passing through each pixel on an image reconstruction plane can be predicted properly upon image reconstruction. Therefore, the image reconstruction can be carried out accurately.

There is provided an X-ray CT apparatus according to a fourth aspect, wherein in the X-ray CT apparatus according to any of the first to third aspects, an X-ray data acquisition system has X-ray data acquisition device which records at least one of at least one absolute coordinate value or relative coordinate value of a scanning table z-direction coordinate position, a scanning table x-direction coordinate position, a scanning table y-direction coordinate position, a scanning gantry rotating section rotation-angle position, a scanning gantry tilt angle position, a scanning gantry x-direction coordinate position, a scanning gantry y-direction coordinate position, and a scanning gantry z-direction coordinate position.

In order to solve the above problems, in the X-ray CT apparatus according to the fourth aspect, the operation parameters set by the scanning gantry, and the X-ray data acquisition device and scanning table lying thereinside are recorded using the absolute coordinate value and the relative coordinate value when the operation parameters are recorded in the third aspect. Since the position of an X-ray beam passing through each pixel on an image reconstruction plane can be properly predicted absolutely or relatively upon image reconstruction, the image reconstruction can be carried out accurately.

In order to solve the above problems, there is provided an X-ray CT apparatus according to a fifth aspect, wherein in the X-ray CT apparatus according to any of the first to fourth aspects, an X-ray data acquisition system has X-ray data acquisition device which records at least one of at least one absolute coordinate value or relative coordinate value of a scanning table z-direction coordinate position, a scanning table x-direction coordinate position, a scanning table y-direction coordinate position, a scanning gantry rotating section rotation-angle position, a scanning gantry tilt angle position, a scanning gantry x-direction coordinate position, a scanning gantry y-direction coordinate position, and a scanning gantry z-direction coordinate position and adds the same to X-ray projection data.

In the X-ray CT apparatus according to the fifth aspect, when the operation parameters set by the scanning gantry, and the X-ray data acquisition device and scanning table lying thereinside are recorded in the third or fourth aspect, they are recoded with being added to X-ray projection data. It is thus unnecessary to associate the operation parameters with another file where they are set as another file. Therefore, the operation of the X-ray data acquisition device can be predicted on software of an image reconstruction device according to a simpler file operation upon image reconstruction. Further, the position of an X-ray beam passing through each pixel on an image reconstruction plane can properly be predicted upon image reconstruction. It is therefore possible to carry out the image reconstruction accurately.

In order to solve the above problems, there is provided an X-ray CT apparatus according to a sixth aspect, wherein in the X-ray CT apparatus according to any of the first to fifth aspects, the X-ray data acquisition device records at least one of accelerations or decelerations about operations in a scanning table z direction, a scanning table x direction, a scanning table y direction, a scanning gantry rotating section rotation-angle direction, a scanning gantry tilt angle direction, a scanning gantry x-direction angle direction, a scanning gantry y-direction angle direction and a scanning gantry z-direction angle direction of an X-ray data acquisition system.

In the X-ray CT apparatus according to the sixth aspect, the acceleration and deceleration at each time are contained in the operation parameters set by the scanning gantry corresponding to the X-ray data acquisition device, and the X-ray data acquisition device thereinside and scanning table lying in the first to fifth aspects. Since the velocities and travel distances for the operations are known from this point, the prediction of the operations can be carried out properly. Thus, since the position of an X-ray beam passing through each pixel on an image reconstruction plane can be properly predicted upon image reconstruction, the image reconstruction can be carried out accurately.

In order to solve the above problems, there is provided an X-ray CT apparatus according to a seventh aspect, wherein in the X-ray CT apparatus according to any of the first to sixth aspects, the X-ray data acquisition device records at least one of initial positions, stop positions, acceleration end positions or deceleration start positions about operations in a scanning table z direction, a scanning table x direction, a scanning table y direction, a scanning gantry rotating section rotation-angle direction, a scanning gantry tilt angle direction, a scanning gantry x-direction angle direction, a scanning gantry y-direction angle direction and a scanning gantry z-direction angle direction of an X-ray data acquisition system.

In the X-ray CT apparatus according to the seventh aspect, the initial positions, stop positions, acceleration end positions or deceleration start positions about the operations are contained in the operation parameters set by the scanning gantry corresponding to the X-ray data acquisition device, and the X-ray data acquisition device and scanning table lying thereinside in the first to sixth aspects. From this point, the position of the X-ray data acquisition system is known in combination with the acceleration and deceleration, so the prediction of the operations can be carried out properly. Thus, since the position of an X-ray beam passing through each pixel on an image reconstruction plane can be predicted properly upon image reconstruction, the image reconstruction can be carried out accurately.

In order to solve the above problems, there is provided an X-ray CT apparatus according to an eighth aspect, wherein in the X-ray CT apparatus according to any of the first to seventh aspects, the X-ray data acquisition device records stationary velocities about operations in a scanning table z direction, a scanning table x direction, a scanning table y direction, a scanning gantry rotating section rotation-angle direction, a scanning gantry tilt angle direction, a scanning gantry x-direction angle direction, a scanning gantry y-direction angle direction and a scanning gantry z-direction angle direction of an X-ray data acquisition system.

In the X-ray CT apparatus according to the eighth aspect, the steady-state or stationary velocities are contained in the operation parameters set by the scanning gantry corresponding to the X-ray data acquisition device, and the X-ray data acquisition device and scanning table lying thereinside in the first to seventh aspects. From this point, the position of the X-ray data acquisition system can be reconfirmed, and the prediction of each operation reduced in error can be carried out properly. Thus, since the position of an X-ray beam passing through each pixel on an image reconstruction plane can be predicted properly upon image reconstruction, the image reconstruction can be carried out accurately.

In order to solve the above problems, there is provided an X-ray CT apparatus according to a ninth aspect, wherein in the X-ray CT apparatus according to any of the first to eighth aspects, when X-ray projection data corresponding to respective views are image-reconstructed, the image reconstructing device reproduces position information of an X-ray data acquisition system to perform image reconstruction.

In the X-ray CT apparatus according to the ninth aspect, there is a need to reproduce the position information of the X-ray data acquisition system by the operation parameters upon image reconstruction in the first to eighth aspects. Thus, since the position of an X-ray beam passing through each pixel on an image reconstruction plane can be predicted properly upon image reconstruction, the image reconstruction can be performed accurately.

In order to solve the above problems, there is provided an X-ray CT apparatus according to a tenth aspect, wherein in the X-ray CT apparatus according to any of the first to ninth aspects, the operations of an X-ray data acquisition system about a scanning table z direction, a scanning table x direction, a scanning table y direction, a scanning gantry rotating section rotation-angle direction, a scanning gantry tilt angle direction, a scanning gantry x-direction angle direction, a scanning gantry y-direction angle direction and a scanning gantry z-direction angle direction of an X-ray data acquisition system are linear control.

In the X-ray CT apparatus according to the tenth aspect, the operations of the scanning gantry corresponding to the X-ray data acquisition device, and the X-ray data acquisition device and scanning table lying thereinside are linearly-controlled. Consequently, the prediction of the operations becomes simple and hence the burden on a control system is reduced. Thus, since the position of an X-ray beam passing through each pixel on an image reconstruction plane can be predicted properly upon image reconstruction, the image reconstruction can be carried out accurately.

In order to solve the above problem, there is provided an X-ray CT apparatus according to an eleventh aspect, wherein in the X-ray CT apparatus according to any of the first to ninth aspects, the operations of an X-ray data acquisition system about a scanning table z direction, a scanning table x direction, a scanning table y direction, a scanning gantry rotating section rotation-angle direction, a scanning gantry tilt angle direction, a scanning gantry x-direction angle direction, a scanning gantry y-direction angle direction and a scanning gantry z-direction angle direction of an X-ray data acquisition system are nonlinear control.

In the X-ray CT apparatus according to the eleventh aspect, the operations of the scanning gantry corresponding to the X-ray data acquisition device, and the X-ray data acquisition device and scanning table lying thereinside are nonlinearly-controlled. Consequently, the discontinuity of acceleration can be eliminated and hence smoother operations can be taken. In particular, it is preferable to use the scanning table because it gives a softer operation to a subject placed thereon. Since the position of an X-ray beam passing through each pixel on an image reconstruction plane can properly be predicted upon image reconstruction even in this case, the proper image reconstruction can be carried out.

In order to solve the above problems, there is provided an X-ray CT apparatus according to a twelfth aspect, wherein in the X-ray CT apparatus according to any of the first to eleventh aspects, the image reconstructing device performs three-dimensional image reconstruction as image reconstruction.

In the X-ray CT apparatus according to the twelfth aspect, the three-dimensional image reconstruction is used to perform image reconstruction properly after the X-ray beam passing through each pixel on the image reconstruction plane is properly predicted upon image reconstruction in the first to eleventh aspects. Consequently, each X-ray projection data is backprojected on its corresponding proper position as viewed in the z direction and hence the photography or imaging of a tomographic image reduced in artifact and good in image quality can be realized.

In order to solve the above problems, there is provided an X-ray CT apparatus according to a thirteenth aspect, wherein in the X-ray CT apparatus according to any of the first to twelfth aspects, the X-ray data acquisition device records at least one of an initial value, a completion value, an acceleration value, a deceleration value and a constant value with respect to at least one imaging condition of an X-ray tube voltage, an X-ray tube current, a scan velocity, an X-ray collimator aperture or open width and an X-ray collimator open position.

In the X-ray CT apparatus according to the thirteenth aspect, even at executing portions of continuous operations, operations and changes, of an X-ray data acquisition system related to a mechanism system or an analog electric circuit, such as the X-ray tube voltage, X-ray tube current, scan velocity, X-ray collimator open width and X-ray collimator open position, the operations of the portions can be predicted and described with operation parameters when operated in X-ray data acquisition during photography in a manner similar to the prediction of the z-direction position of the scanning table, the prediction of the scanning gantry tilt angle and the like. Executing image reconstruction in consideration of the operations upon image reconstruction at this time enables proper image reconstruction.

In order to solve the above problems, there is provided an X-ray CT apparatus according to a fourteenth aspect, wherein in the X-ray CT apparatus according to any of the first to thirteenth aspects, the X-ray data acquisition device adds at least one of an initial value, a completion value, an acceleration value, a deceleration value and a constant value to X-ray projection data and records the result of addition therein, with respect to at least one imaging condition of an X-ray tube voltage, an X-ray tube current, a scan velocity, a view data acquisition sampling frequency, the number of data acquisition channels and the number of data acquisition rows.

In the X-ray CT apparatus according to the fourteenth aspect, the continuous operations, operations and changes of the X-ray data acquisition system can be described with their corresponding operation parameters, and the operation parameters can be recorded with being added to the X-ray projection data in the thirteenth aspect. Thus, image reconstruction can be executed properly by performing the image reconstruction in consideration of the operations upon the image reconstruction.

According to the present invention, an X-ray CT apparatus can be realized which is capable of efficiently storing position information and photography or imaging information of an X-ray data acquisition system.

BRIEF DESCRIPTION OF THE DRAWINGS

FIG. 9 is a conceptual diagram illustrating lines projected onto an X-ray detector plane.

FIG. 16 is a diagram showing a relationship between scanning table position information and data acquisition view numbers.

FIG. 19 is a diagram depicting operation parameters of the scanning table (cradle) at the helical shuttle scan.

DETAILED DESCRIPTION OF THE INVENTION

The present invention will hereinafter be explained in further detail by embodiments illustrated in the figures. Incidentally, the present invention is not limited to or by the embodiments.

[Apparatus Construction]

Figure 1:
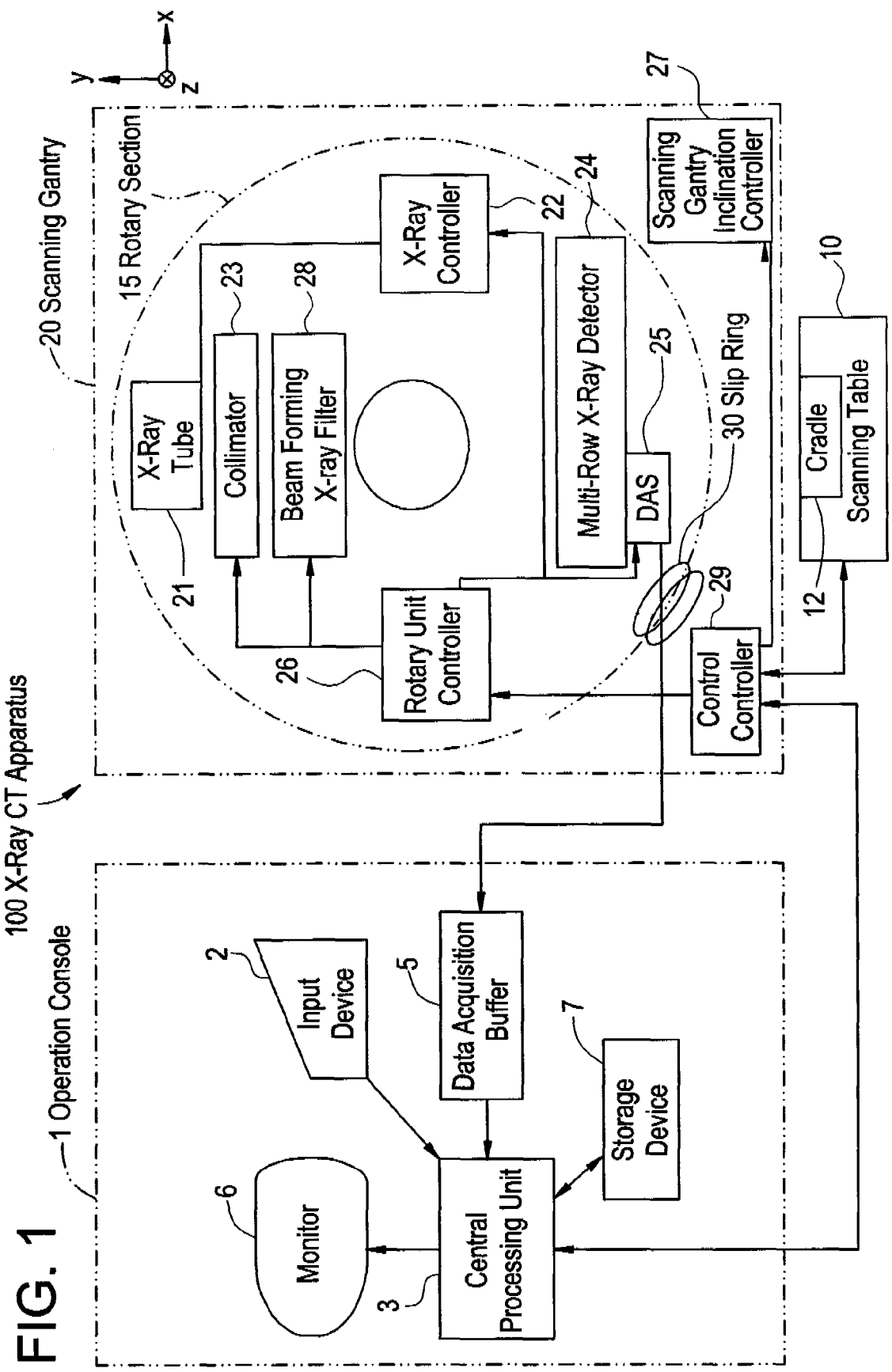
FIG. 1 is a block diagram showing an X-ray CT apparatus according to a first embodiment of the present invention.

FIG. 1 is a block diagram of an X-ray CT apparatus according to a first embodiment of the present invention.

As shown in FIG. 1, the X-ray CT apparatus 100 according to the present embodiment is equipped with an operation console 1, an imaging or scanning table 10 and a scanning gantry 20.

Figure 14:
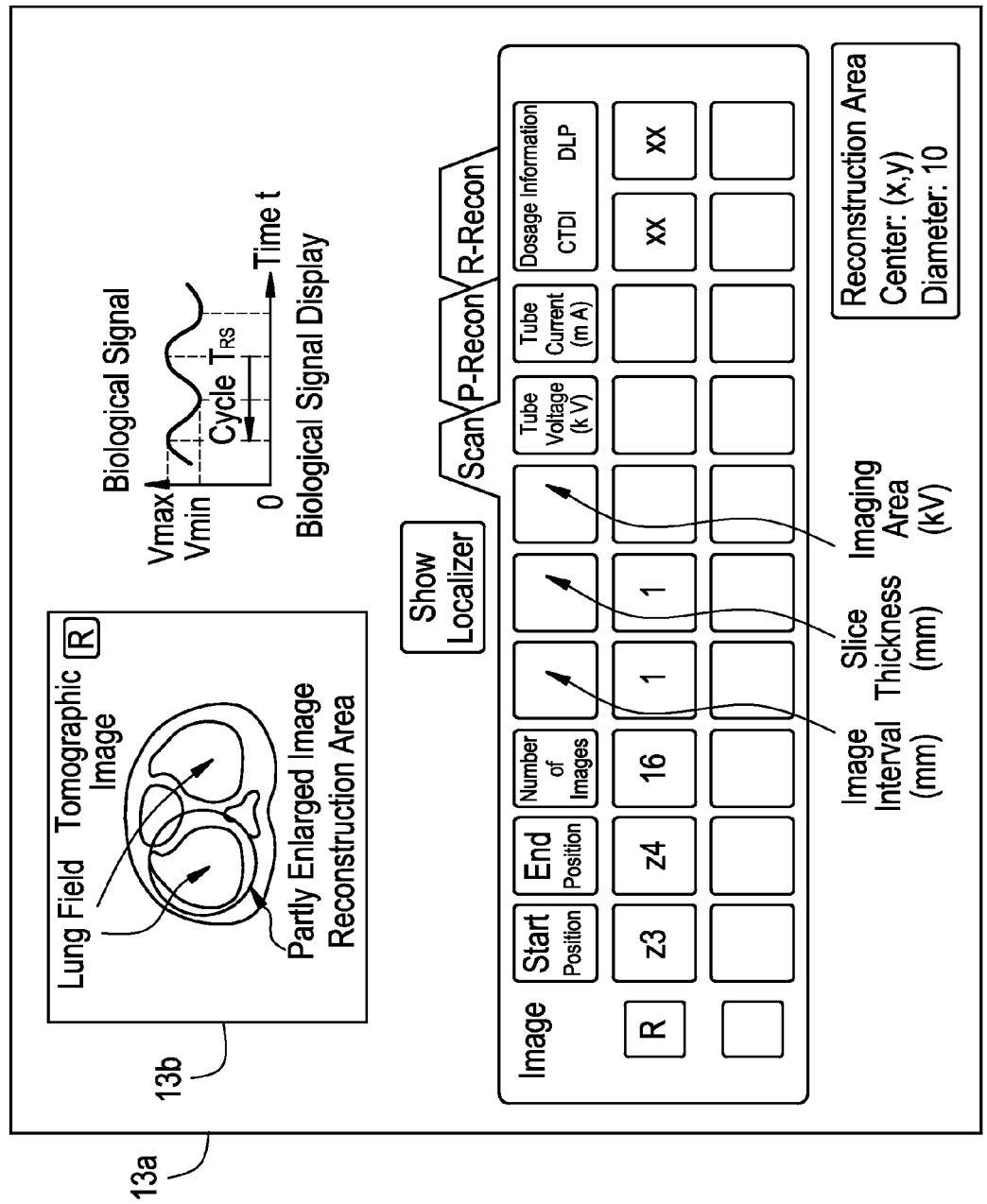
FIG. 14 is a diagram showing an imaging condition input screen of the X-ray CT apparatus.

As shown in FIG. 1, the operation console 1 includes an input device 2 which receives an input from an operator, a central processing unit 3 which executes data processing such as a pre-process, an image reconstructing process, a post-process, etc. a data acquisition buffer 5 which acquires or collects X-ray detector data acquired by the scanning gantry 20, a monitor 6 which displays a tomographic image image-reconstructed from projection data obtained by pre-processing the X-ray detector data, and a memory or storage device 7 which stores programs, X-ray detector data, projection data and X-ray tomographic images therein. In the present embodiment, an input for imaging or photographing conditions is inputted from the input device 2 and stored in the storage device 7. An example of an imaging condition input screen is shown in FIG. 14.

As shown in FIG. 1, the scanning table 10 includes a cradle 12 which inserts and draws a subject into and from a bore or aperture of the scanning gantry 20 with the subject placed thereon. Although not shown in the figure in particular, the cradle 12 is elevated and moved linearly on the scanning table 10 by a motor built in the scanning table 10.

Figure 2:
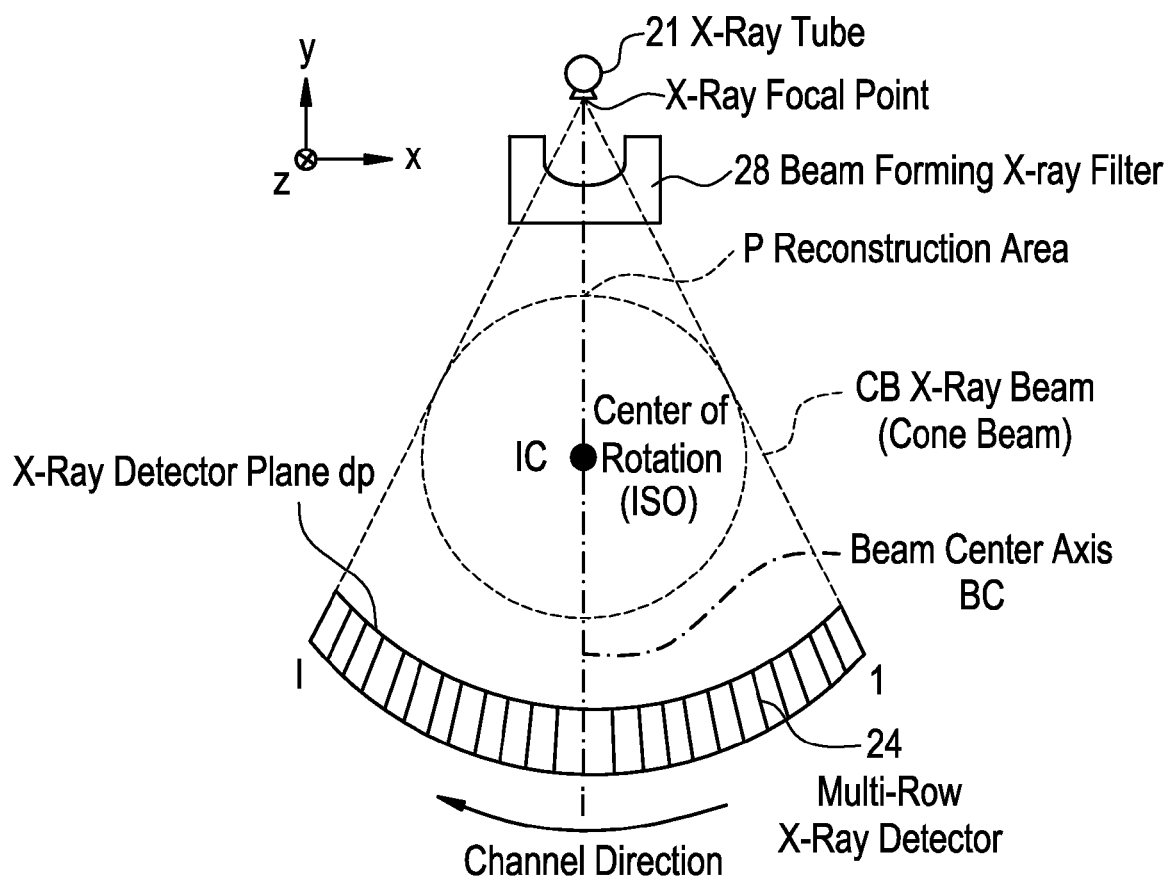
FIG. 2 is an explanatory diagram showing an X-ray generator (X-ray tube) and a multi-row X-ray detector as viewed in an xy plane.

As shown in FIG. 1, the scanning gantry 20 includes an X-ray tube 21, an X-ray controller 22, a collimator 23, a beam forming X-ray filter 28, a multi-row X-ray detector 24, a DAS (Data Acquisition System) 25, a rotating section controller 26 which controls the X-ray tube 21 or the like that are mounted on a rotating section 15 so as to be rotated about a body axis of the subject, and a control controller 29 which swaps control signals or the like with the operation console 1 and the scanning table 10. Here, the beam forming X-ray filter 28 is configured so as to be thinnest in thickness as viewed in the direction of X rays directed to the center of rotation corresponding to the center of imaging, to increase in thickness toward its peripheral portion and to be able to further absorb the X rays as shown in FIG. 2. Therefore, in the present embodiment, the body surface of a subject whose sectional shape is nearly circular or elliptic can be less exposed to radiation. The scanning gantry 20 can be tiled about ±30° or so forward and rearward as viewed in the z direction by a scanning gantry tilt controller 27.

The X-ray tube 21 and the multi-row X-ray detector 24 are rotated about the center of rotation IC as shown in FIG. 2. Assuming that the vertical direction is a y direction, the horizontal direction is an x direction and the travel direction of the table and cradle orthogonal to these is a z direction, the plane at which the X-ray tube 21 and the multi-row X-ray detector 24 are rotated, is an xy plane. The direction in which the cradle 12 is moved, corresponds to the z direction.

Figure 3:
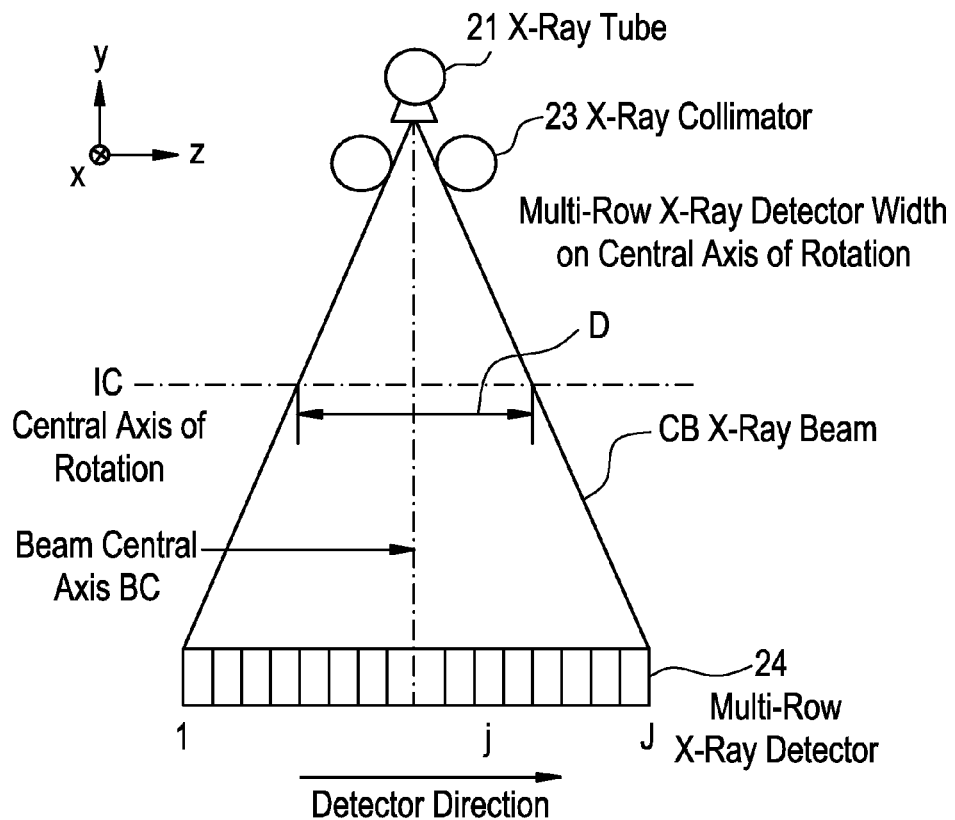
FIG. 3 is an explanatory diagram illustrating the X-ray generator (X-ray tube) and the multi-row X-ray detector as viewed in a yz plane.

FIGS. 2 and 3 are explanatory diagrams showing a geometrical arrangement or layout of the X-ray tube 21 and the multi-row X-ray detector 24 as viewed from the xy plane or yz plane.

As shown in FIG. 2, the X-ray tube 21 generates an X-ray beam called a cone beam CB. Incidentally, when the direction of a central axis of the cone beam CB is parallel to the y direction, this is defined as a view angle 0°.

As shown in FIG. 2, the multi-row X-ray detector 24 has X-ray detector rows arranged in plural form in the z direction and has, for example, X-ray detector rows corresponding to 256 rows. Each of the X-ray detector rows has X-ray detector channels corresponding to, for example, 1024 channels as viewed in a channel direction.

As shown in FIG. 2, the X-ray beam emitted from an X-ray focal point of the X-ray tube 21 is spatially controlled in X-ray dosage by the beam forming X-ray filter 28 in such a manner that more X rays are radiated in the center of a reconstruction area or plane P and less X rays are radiated at a peripheral portion of the reconstruction area P. Thereafter, the X rays are absorbed by the subject that exists inside the reconstruction area P, and the X rays transmitted through the subject are acquired by the multi-row X-ray detector 24 as X-ray detector data.

As shown in FIG. 3, the X-ray beam emitted from the X-ray focal point of the X-ray tube 21 is controlled in the direction of a slice thickness of a tomographic image by the X-ray collimator 23. That is, the X-ray beam is controlled in such a manner that the width of the X-ray beam becomes D at a central axis of rotation IC. Then, the X rays are absorbed into the subject existing in the vicinity of the central axis of rotation IC, and the X rays transmitted through the subject are acquired by the multi-row X-ray detector 24 as X-ray detector data.

Thus, the projection data acquired by application of the X rays are outputted from the multi-row X-ray detector 24 to the DAS 25 and A/D converted by the DAS 25. Then, the data are inputted to the data acquisition buffer 5 via a slip ring 30. Thereafter, the data inputted to the data acquisition buffer 5 are processed by the central processing unit 3 in accordance with the corresponding program stored in the storage device 7, so that the data are image-reconstructed as a tomographic image. Afterwards, the tomographic image is displayed on a display screen of the monitor 6.

Outline of Operations

The outline of each operation of the X-ray CT apparatus 100 is shown below.

Figure 4:
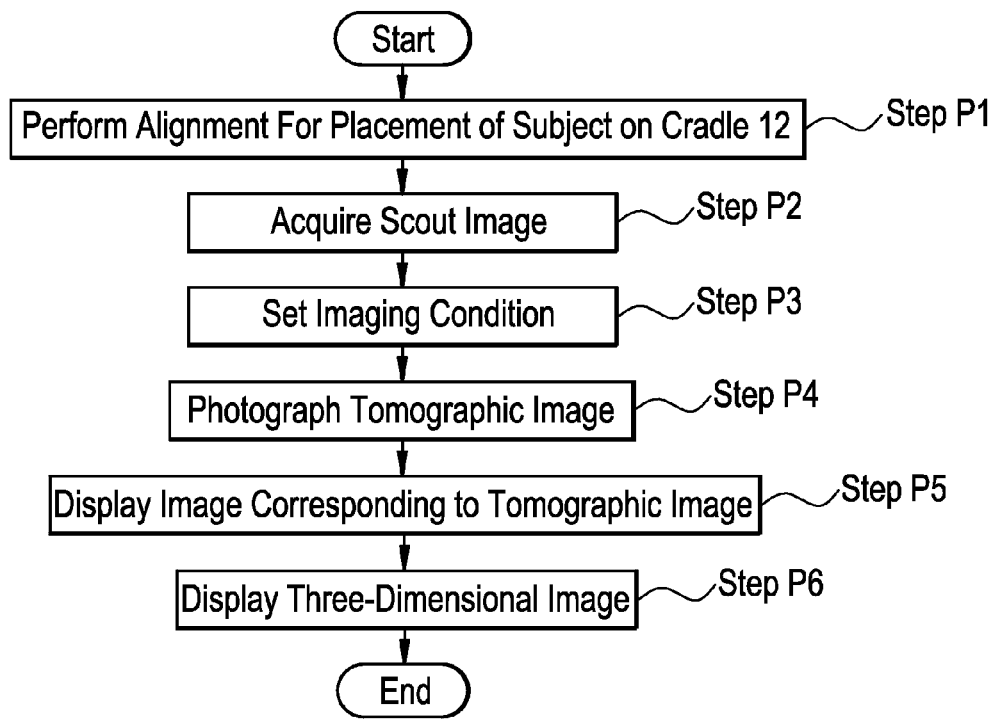
FIG. 4 is a flow chart depicting the flow of subject imaging.

FIG. 4 is a flow chart showing the outline of the operations of the X-ray CT apparatus according to the present embodiment.

At Step P1, as shown in FIG. 4, the subject is first placed on the cradle 12 and its alignment is made.

Here, a slice light center position of the scanning gantry 20 is aligned with a reference point of each region of the subject placed on the cradle 12.

Next, at Step P2, scout image acquisition is performed as shown in FIG. 4.

Here, a scout image is normally photographed at view angles of 0° and 90°. Incidentally, only a 90° scout image may be photographed or imaged as in the case of, for example, the head, depending upon each region. The details of the photographing of the scout image will be described later.

Next, at Step P3, an imaging or photographing condition is set as shown in FIG. 4.

Here, the imaging condition is normally set while the position and size of a tomographic image to be photographed are being displayed on a scout image. In this case, the whole X-ray dosage information corresponding to one helical scan, variable-pitch helical scan, helical shuttle scan, conventional scan (axial scan) or cine scan is displayed. When the number of rotations of a scanning gantry rotating section (an X-ray data acquisition system) or the set value of imaging (X-ray application) time is inputted upon the cine scan, X-ray dosage information corresponding to the inputted number of rotations in the area of interest of the subject or the time inputted is displayed.

Figure 5:
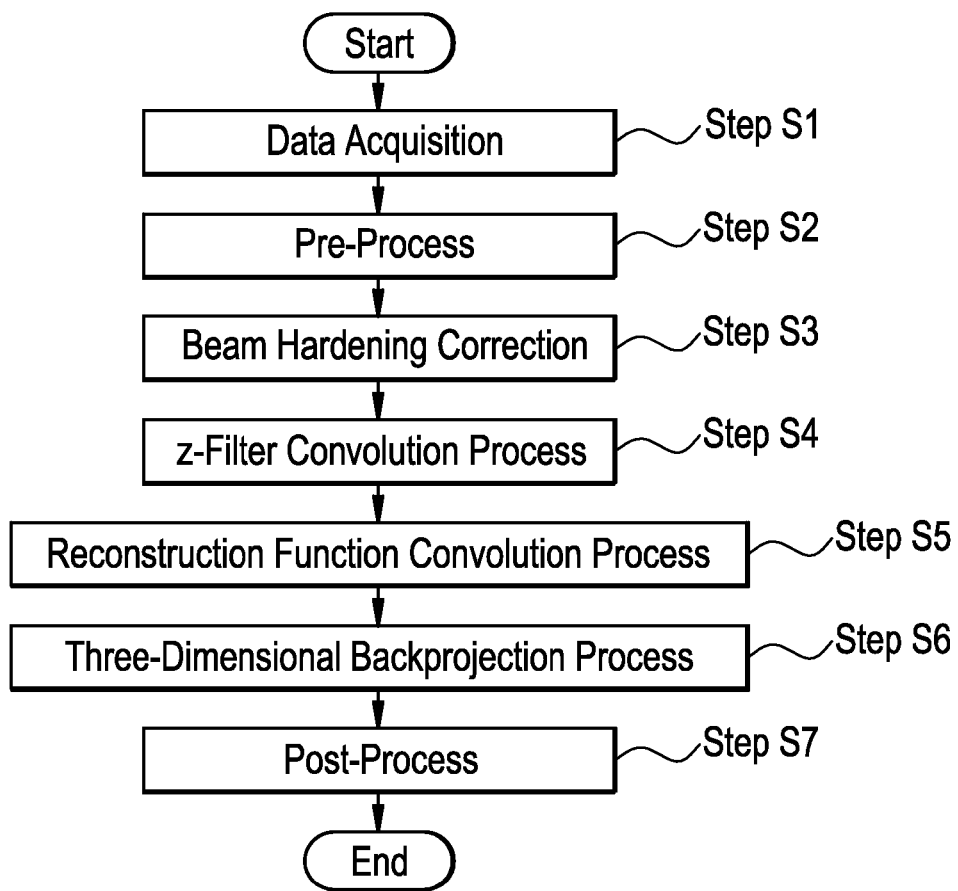
FIG. 5 is a flow chart showing a schematic operation for image reconstruction, of the X-ray CT apparatus according to the first embodiment of the present invention.
Figure 7:
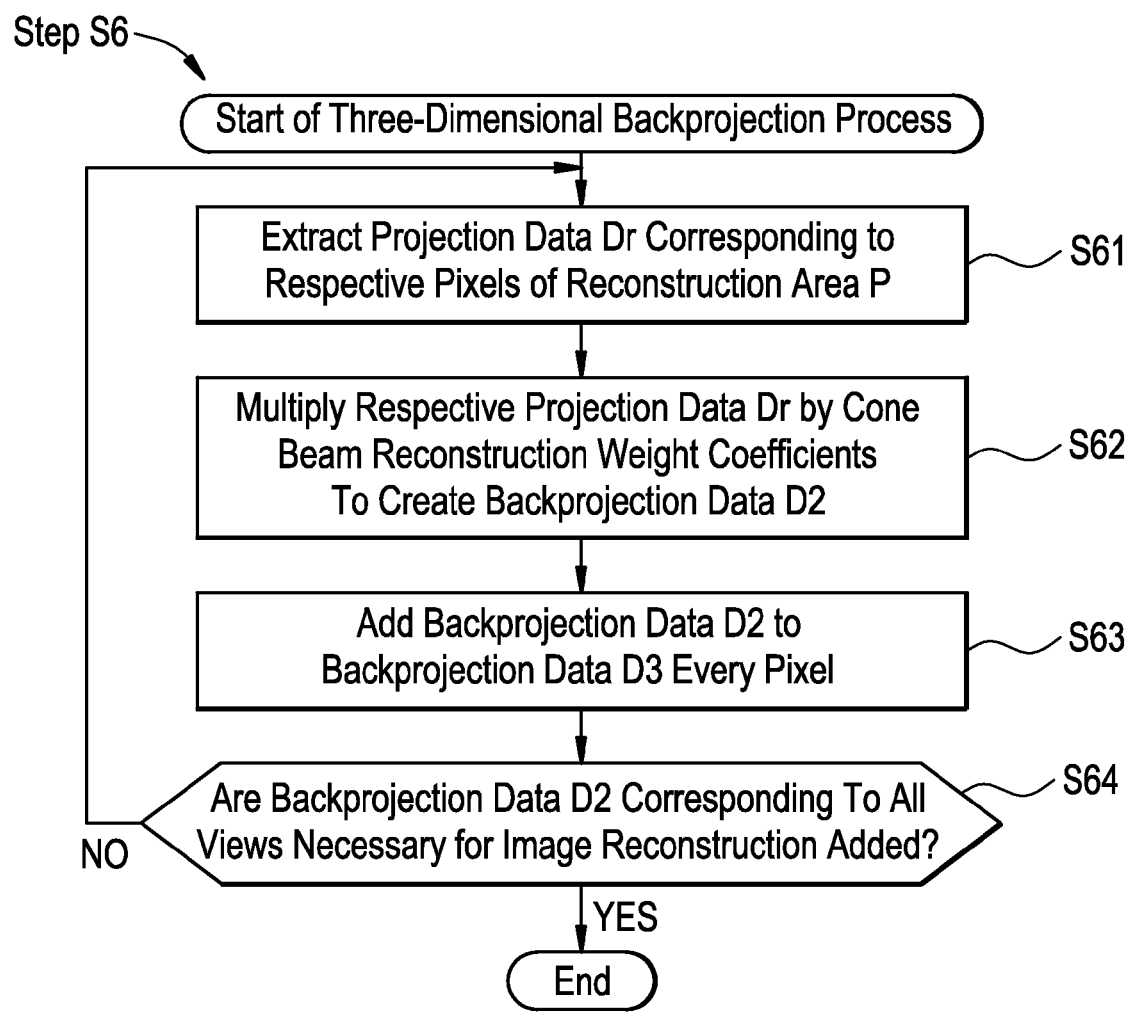
FIG. 7 is a flow chart depicting the details of a three-dimensional image reconstructing process.

Upon setting of an imaging condition for the helical shuttle scan or the variable-pitch helical scan, operation parameters for performing z-direction operation control can be defined at the scanning table. These operation parameters are determined upon the setting of the imaging condition and sent to a scanning table control section to actually operate the scanning table. Then, these operation parameters are added to X-ray projection data. Upon image reconstruction, the position of an X-ray beam passing through each pixel on an image reconstruction plane is properly predicted in consideration of such an operation to perform proper three-dimensional image reconstruction. This image reconstruction will be explained in detail in FIG. 5 shown below. The three-dimensional image reconstruction will be described in detail in FIG. 7 shown below.

The details of the operation parameters for the helical shuttle scan or the variable-pitch helical scan will also be explained later.

Next, at Step P4, tomographic image photography is performed as shown in FIG. 4.

The details of the tomographic image photography and the image reconstruction will be described later.

Next, at Step P5, an image-reconstructed tomographic image is displayed as shown in FIG. 4.

Next, at Step P6, a three-dimensional image display is performed as shown in FIG. 4.

Figure 15:
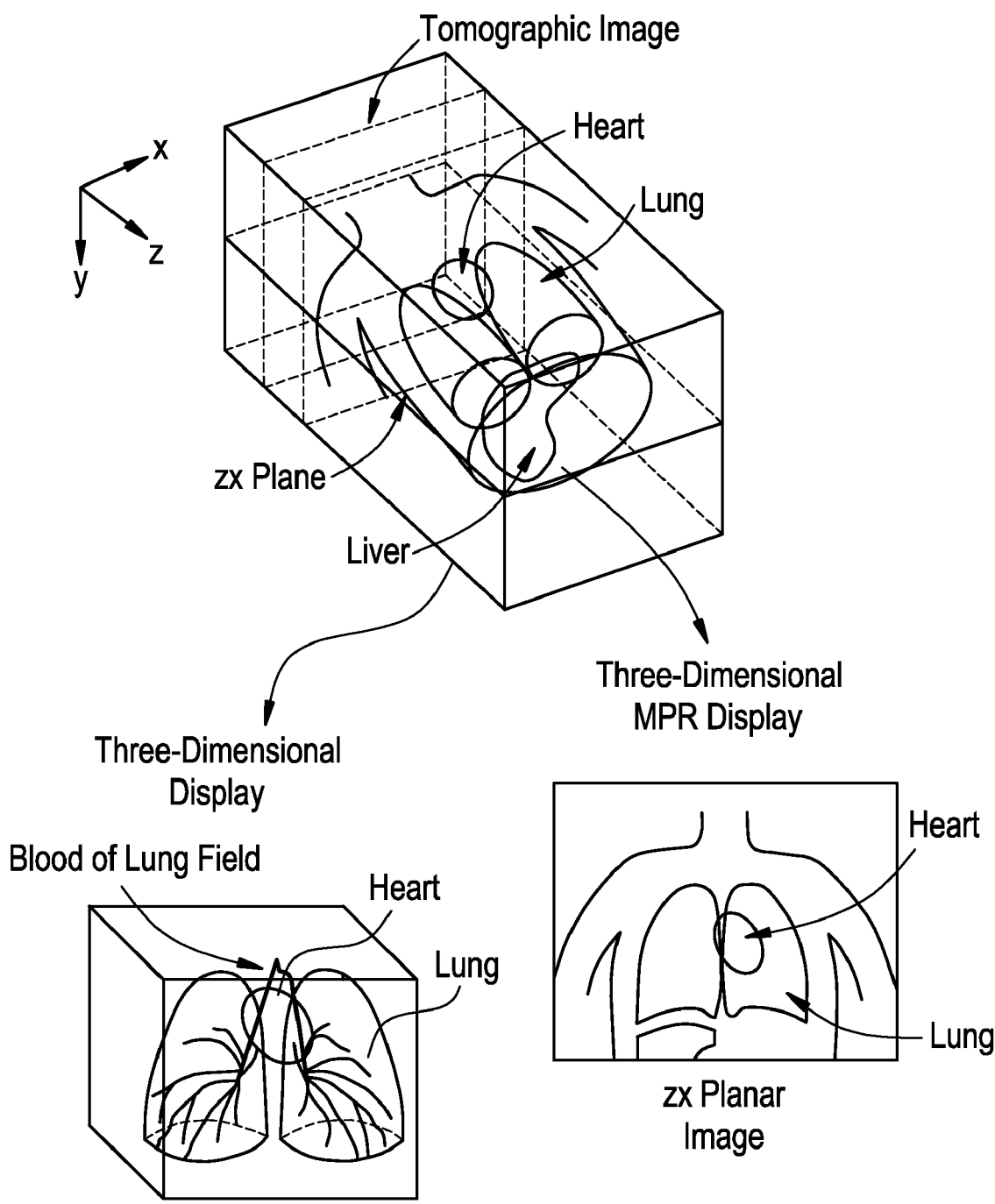
FIG. 15 is a diagram showing an example illustrative of a three-dimensional MPR display and a three-dimensional display.

Here, a tomographic image photographed continuously in a z direction is used as a three-dimensional image and three-dimensionally image-displayed as shown in FIG. 15.

As methods for the three-dimensional image display, may be mentioned, a volume rendering three-dimensional image display method, an MIP (Maximum Intensity Projection) image display method, an MPR (Multi Plain Reformat) image display method, a three-dimensional reprojection image display method, etc. They are used properly according to diagnostic applications.

[Outline of Operations at Tomographic Image Photography and scout Image Photography]

The outline of operations of the X-ray CT apparatus 100 at the execution of tomographic image photography (Step P4 in FIG. 4) and scout image photography (Step P2 in FIG. 4) upon will be shown below.

FIG. 5 is a flow chart showing the outline of the operations for the tomographic image photography and scout image photography, of the X-ray CT apparatus 100 of the embodiment according to the present invention.

At Step S1, data acquisition is first performed as shown in FIG. 5.

When the data acquisition is carried out by a helical scan upon executing the tomographic image photography, the operation of rotating the X-ray tube 21 and the multi-row X-ray detector 24 about the subject and carrying out data acquisition of X-ray detector data while the cradle 12 placed on the imaging or scanning table 10 is being linearly moved, is performed. Upon the helical scan for acquiring or collecting the X-ray detector data, data acquisition in a constant-speed range is performed.

Upon a variable-pitch helical scan or a helical shuttle scan, data acquisition is performed even at acceleration and deceleration in addition to the data acquisition in the constant-speed range. In this case, scanning table z-direction operation parameters predicted by the central processing unit 3 including imaging condition setting device are added to X-ray detector data D0 (view, j, i) indicated by a view angle view, a detector row number j and a channel number i.

Figure 17:
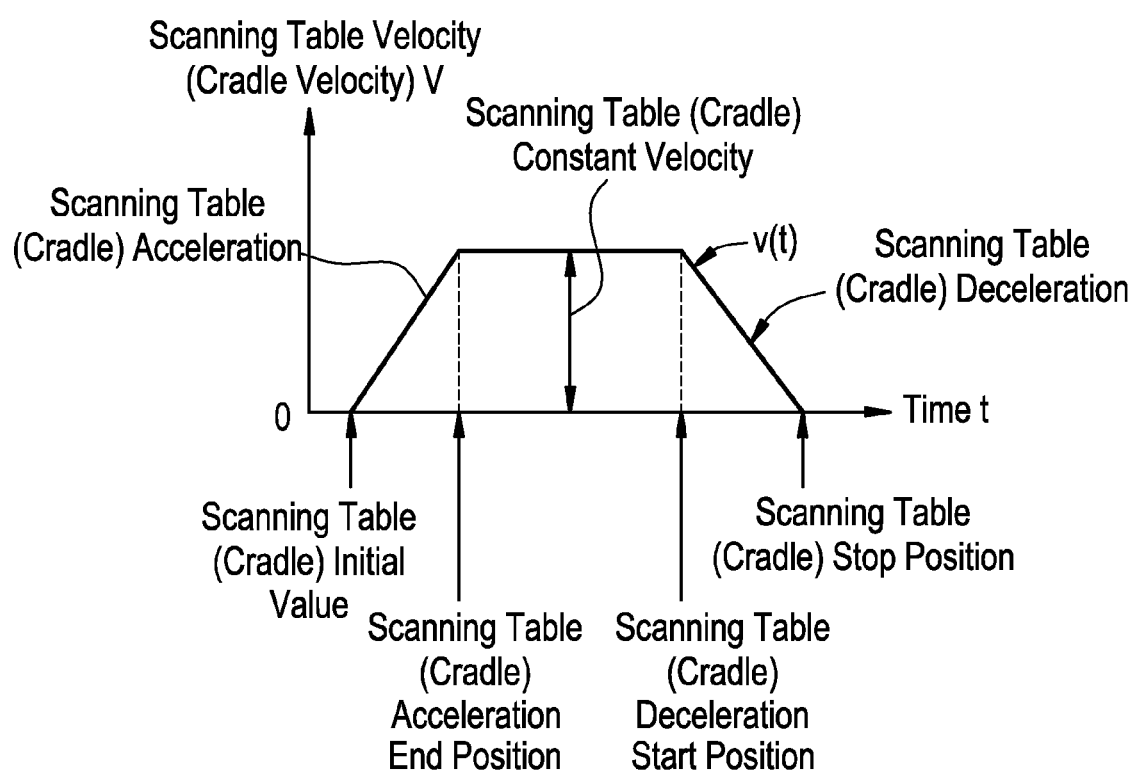
FIG. 17 is a diagram showing operations of a scanning table (cradle) at a helical shuttle scan.

FIG. 17 is a diagram showing operations of the scanning table (cradle) at the helical shuttle scan.

FIG. 17 describes the manner in which the scanning table is moved in the z direction. If parameters like, for example, cradle acceleration, cradle deceleration, a cradle stationary speed or velocity, a cradle initial position, a cradle stop position, a cradle acceleration end position and a cradle deceleration start position exist as shown in FIG. 17 here, then the operations of the scanning table can be described.

If the scanning gantry and the scanning table corresponding to the X-ray data acquisition system can be moved with sufficient accuracy as predicted based on the parameters, it is then unnecessary to subject information about a scanning table z-direction coordinate position, a scanning table x-direction coordinate position, a scanning table y-direction coordinate position, a scanning gantry rotating section rotation-angle position, a scanning gantry tilt angle position, a scanning gantry x-direction coordinate position, a scanning gantry y-direction coordinate position, and a scanning gantry z-direction coordinate position set for each view to measurement, data acquisition and addition to X-ray projection data.

Upon the conventional scan (axial scan) or the cine scan, the data acquisition system is rotated once or plural times while the cradle 12 placed on the scanning table 10 is being fixed to a given z-direction position, thereby to perform data acquisition of X-ray detector data. The cradle 12 is moved to the next z-direction position as needed and thereafter the data acquisition system is rotated once or plural times again to perform data acquisition of X-ray detector data.

On the other hand, upon execution of the scout image photography, the operation of fixing the X-ray tube 21 and the multi-row X-ray detector 24 and performing data acquisition of X-ray detector data while the cradle 12 placed on the scanning table 10 is being linearly moved, is performed.

Next, at Step S2, a pre-process is performed as shown in FIG. 5.

Figure 6:
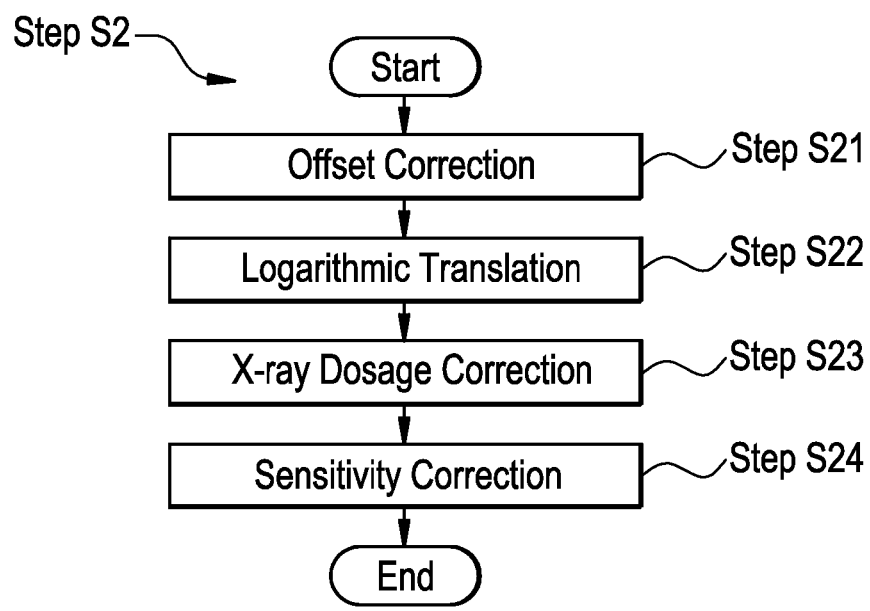
FIG. 6 is a flow chart illustrating the details of a pre-process.

Here, the pre-process is performed on the X-ray detector data D0 (view, j, i) to convert it into projection data. As shown in FIG. 6, the pre-process comprises an offset correction of Step S21, logarithmic translation of Step S22, an X-ray dosage correction of Step S23 and a sensitivity correction of Step S24.

Upon the scout image photography, the pre-processed X-ray detector data is displayed with each of a pixel size in the channel direction and a pixel size in the z direction corresponding to the cradle linear moving direction being made coincident with a display pixel size of the monitor 6.

Next, at Step S3, a beam hardening correction is performed as shown in FIG. 5.

Here, the beam hardening correction is effected on the pre-processed projection data D1 (view, j, i). Assuming that upon the beam hardening correction of Step S3, projection data subjected to the sensitivity correction S24 at the pre-process S2 is defined as D1 (view, j, i) and data subsequent to the beam hardening correction of Step S3 is defined as D11 (view, j, i), the beam hardening correction is expressed in the form of, for example, a polynomial as given by the following expression (1).

[1]

$$D11(\text{view},j,i)=D1(\text{view},j,i)\cdot(B_0(j,i)+B_1(j,i)\cdot D1(\text{view},j,i)+B_2(j,i)\cdot D1(\text{view},j,i)^2) \quad \text{(Expression 1)}$$

Since, at this time, the independent beam hardening corrections can be carried out for every j row of the detectors, the difference between X-ray energy characteristics of the detectors placed for every row can be corrected if tube voltages of respective data acquisition systems are different on the imaging condition.

Next, at Step S4, a z-filter convolution process is performed as shown in FIG. 5.

Here, the z-filter convolution process for applying filters in the z direction (row direction) is effected on the projection data D11 (view, j, i) subjected to the beam hardening correction.

That is, after the pre-process at each view angle and each data acquisition system, projection data of the multi-row X-ray detector D11 (view, j, i) (where i=1 to CH and j=1 to ROW) subjected to the beam hardening correction is multiplied in the row direction by filters in which such row-direction filter sizes as expressed in the following expressions (2) and (3) are five rows, for example. However, (the expression 3) is satisfied.

$$(w_1(i), w_2(i), w_3(i), w_4(i), w_5(i)) \quad \text{(Expression 2)}$$

[2]

$$\sum_{k=1}^{5} w_k(i) = 1 \quad \text{(Expression 3)}$$

The corrected detector data D12 (view, j, i) is given as expressed in the following expression (4):

[3]

$$D12(\text{view}, j, i) = \sum_{k=1}^{5}(D11(\text{view}, j+k-3, i)\cdot w_k(j)) \quad \text{(Expression 4)}$$

Incidentally, assuming that the maximum value of the channel is CH and the maximum value of the row is ROW, the following expressions (5) and (6) are established.

[4]

$$D11(\text{view},-1,i)=D11(\text{view},0,i)=D11(\text{view},1,i) \quad \text{(Expression 5)}$$

[5]

$$D11(\text{viw,ROW},i)=D11(\text{view,ROW}+1,i)=D11(\text{view,ROW}+2,i) \quad \text{(Expression 6)}$$

When row-direction filter coefficients are changed for every channel, slice thicknesses can be controlled depending upon the distance from an image reconstruction center. In a tomographic image, its peripheral portion generally becomes thicker in slice thickness than the reconstruction center thereof. Therefore, the row-direction filter coefficients are changed at the central and peripheral portions, and the row-direction filter coefficients are widely changed in width in the neighborhood of a central channel and narrowly changed in width in the neighborhood of a peripheral channel, thereby making it possible to make the slice thickness uniform at both the peripheral portion and the image reconstruction center.

Controlling the row-direction filter coefficients at the central and peripheral channels of the multi-row X-ray detector 24 in this way makes it possible to control the slice thickness at the central and peripheral portions. Thickening the slice thickness slightly by each row-direction filter yields extensive improvements in both artifact and noise. Thus, the degree of the improvement in artifact and the degree of the improvement in noise can also be controlled. That is, it is possible to control the quality of a three-dimensionally image-reconstructed tomographic image in the xy plane. In addition to above, a tomographic image having a thin slice thickness can also be realized by setting row-direction (z-direction) filter coefficients to deconvolution filters.

Next, at Step S5, a reconstruction function convolution process is performed as shown in FIG. 5.

That is, X-ray projection data subjected to the processes up to the (Expression 6) is subjected to Fourier transformation and multiplied by a reconstruction function, followed by being subjected to inverse Fourier transformation. Assuming that upon the reconstruction function convolution process S5, data subsequent to the z filter convolution process is defined as D12, data subsequent to the reconstruction function convolution process is defined as D13, and the convoluting reconstruction function is defined as Kernel(j), the reconstruction function convolution process is expressed as given by the following expression (7):

[6]

$$D13(\text{view},j,i)=D12(\text{view},j,i)*\text{Kernel}(j) \quad \text{(Expression 7)}$$

That is, since the independent reconstruction function convolution process can be performed for every j row of the detectors, the reconstruction function Kernel (j) can correct differences in noise characteristic and resolution characteristic for every row.

Next, at Step S6, a three-dimensional backprojection process is performed as shown in FIG. 5.

Here, the three-dimensional backprojection process is effected on the projection data D13 (view, j, i) subjected to the reconstruction function convolution process to determine backprojection data D3 (x, y, z). An image-reconstructed image is three-dimensionally image-reconstructed on an xy plane corresponding to a plane orthogonal to the z axis. A reconstruction area or plane P to be shown below is assumed to be parallel to the xy plane. The three-dimensional backprojection process will be explained later referring to FIG. 5.

Next, at Step S7, a post-process is performed as shown in FIG. 5.

Here, the post-process including image filter convolution, CT value conversion and the like is effected on the backprojection data D3 (x, y, z) to obtain a CT or tomographic image D31 (x, y).

Assuming that upon the image filter convolution process in the post-process, a tomographic image subsequent to the three-dimensional backprojection is defined as D31 (x, y, z), data subsequent to the image filter convolution is defined as D32 (x, y, z), and a two-dimensional image filter convolved on the xy plane corresponding to a tomographic image plane is defined as Filter(z), the following expression (8) is established.

[7]

$$D32(x,y,z)=D31(x,y,z)*\text{Filter}(z) \quad \text{(Expression 8)}$$

That is, since the independent image filter convolution process can be performed for every j row of the detectors, it is possible to correct differences in noise characteristic and resolution characteristic for every row.

An image space z-direction filter convolution process shown below may be performed after the two-dimensional image filter convolution process. The image space z-direction filter convolution process may be performed before the two-dimensional image filter convolution process. Further, a three-dimensional image filter convolution process may be performed to bring about such an effect as to share both the two-dimensional image filter convolution process and the image space z-direction filter convolution process.

Assuming that upon the image space z-direction filter convolution process, a tomographic image subjected to the image space z-direction filter convolution process is defined as D33 (x, y, z), and a tomographic image subjected to the two-dimensional image filter convolution process is defined as D32 (x, y, z), the following relation (expression 9) is established. However, v(i) becomes such a coefficient row as expressed below (in expression 10) in the form of image space z-direction filter coefficients at which the width in the z direction is 2l+1.

[8]

$$D32(x, y, z) = \sum_{i=-l}^{l} D32(x, y, z+i) \cdot v(i) \quad \text{(Expression 9)}$$

[9]

$$v(-l), v(-l+1), \ldots v(-1), v(0), v(1), \ldots v(l-1), v(l) \quad \text{(Expression 10)}$$

Upon the helical scan, the image space filter coefficient v(i) may be an image space z-direction filter coefficient independent on a z-direction position. However, when the two-dimensional X-ray area detector 24 or the multi-row X-ray detector 24 broad in detector width as viewed in the z direction is used in particular, the image space z-direction filter coefficient v(i) can be subjected to detailed adjustments dependent on row positions of respective tomographic images upon execution of the conventional scan (axial scan) or the cine scan if the image space z-direction filter coefficient v(i) is given as each of image space z-direction filter coefficients dependent on the positions of the rows of the X-ray detector in the z direction. Therefore, this is further effective.

The so-obtained tomographic images are displayed on the monitor 6.

[Three-Dimensional Backprojection Process]

The outline of the operation at the time that the three-dimensional backprojection process is carried out (S6 in FIG. 5) at the operations of the X-ray CT apparatus 100, is shown below.

FIG. 7 is a flow chart showing the details of the three-dimensional backprojection process.

In the present embodiment, an image to be image-reconstructed is three-dimensionally image-reconstructed on an xy plane corresponding to a plane orthogonal to the z axis. That is, the reconstruction area P is assumed to be parallel to the xy plane.

At Step S61, attention is first given to one of all views (i.e., views corresponding to 360° or views corresponding to "180°+fan angles") necessary for image reconstruction of a tomographic image as shown in FIG. 7. Projection data Dr corresponding to respective pixels in a reconstruction area P are extracted.

Figure 8A:
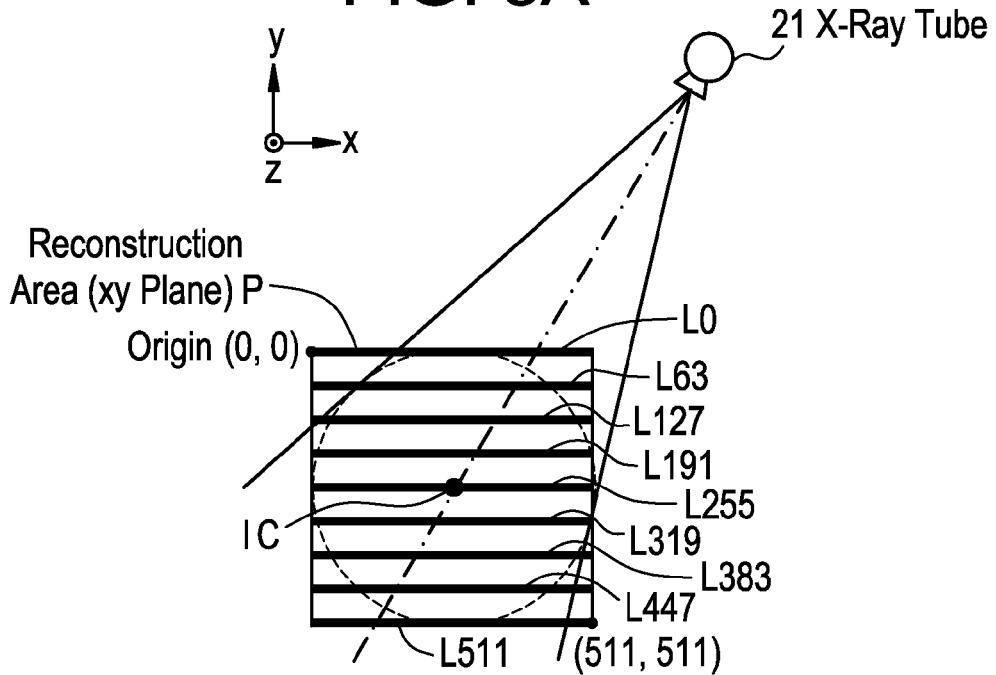
FIGS. 8a and 8b are conceptual diagrams showing a state in which lines on a reconstruction area are projected in an X-ray penetration direction.
Figure 8B:
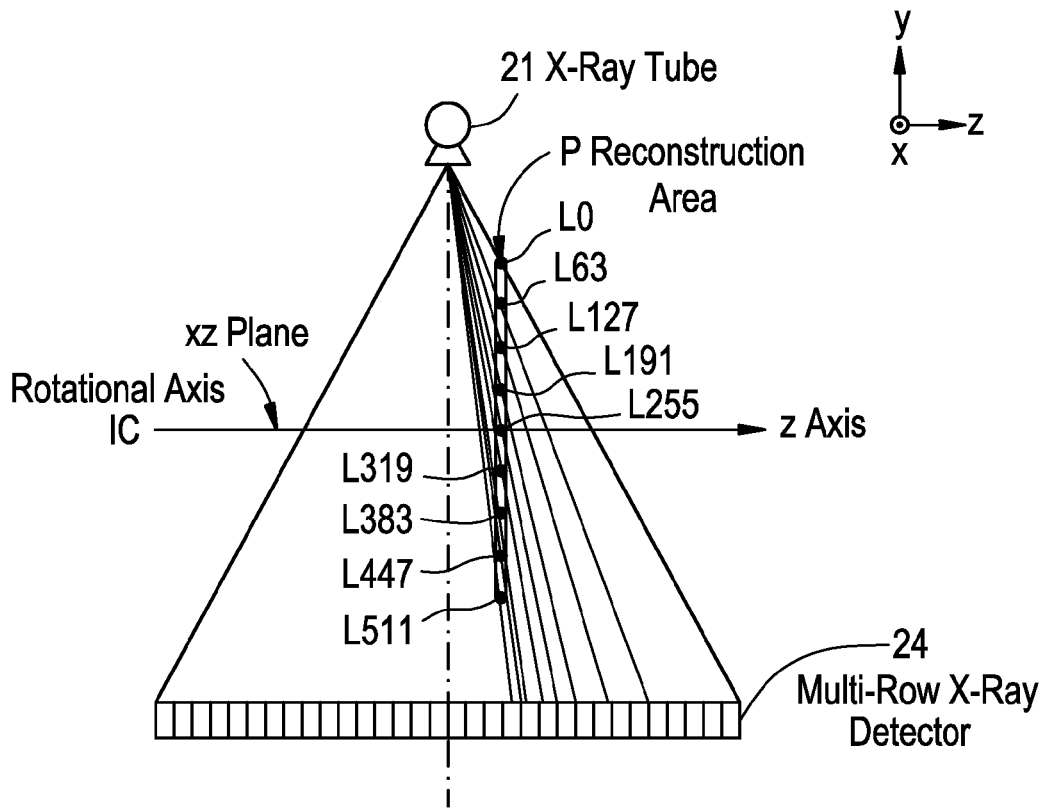

Here, as shown in FIGS. 8(a) and 8(b), a square area of 512×512 pixels, which is parallel to the xy plane, is assumed to be a reconstruction area P. Further, a pixel row L0 parallel to an x axis of y=0, a pixel row L63 of y=63, a pixel row L127 of y=127, a pixel row L191 of y=191, a pixel row L255 of y=255, a pixel row L319 of y=319, a pixel row L383 of y=383, a pixel row L447 of y=447, and a pixel row L511 of y=511 are taken as rows. Thus, if projection data on lines T0 through T511 obtained by projecting these pixel rows L0 to L511 on the plane of the multi-row X-ray detector 24 in an X-ray penetration direction are extracted as shown in FIG. 9, then they result in projection data Dr (view, x, y) of the pixel rows L0 to L511. However, x and y correspond to respective pixels (x, y) of the tomographic image.

The X-ray penetration direction is determined depending on geometrical positions of the X-ray focal point of the X-ray tube 21, the respective pixels and the multi-row X-ray detector 24. However, the operation of the scanning table is predicted for each view from the scanning table operation parameters added to the X-ray detector data. Further, the z coordinates z (view) of X-ray detector data D0 (view, j, i) are determined as the table linear movement z-direction position Ztable (view). Since the z-direction positions of the X-ray focal point and the multi-row X-ray detector in the data acquisition geometrical system are known even in the case of the X-ray detector data D0 (view, j, i) placed under acceleration and deceleration and during a constant velocity, the X-ray penetration direction can be accurately determined by prediction. Thus, three-dimensional image reconstruction for each pixel of a tomographic image can be carried out.

Incidentally, when some of lines are placed out of the multi-row X-ray detector 24 as viewed in the channel direction as in the case of, for example, the line T0 obtained by projecting, for example, the pixel row L0 on the plane of the multi-row X-ray detector 24 in the X-ray penetration direction, the corresponding projection data Dr (view, x, y) is set to "0". When it is placed outside the multi-row X-ray detector 24 as viewed in the z direction, the corresponding projection data Dr (view, x, y) is determined by extrapolation.

Figure 10:
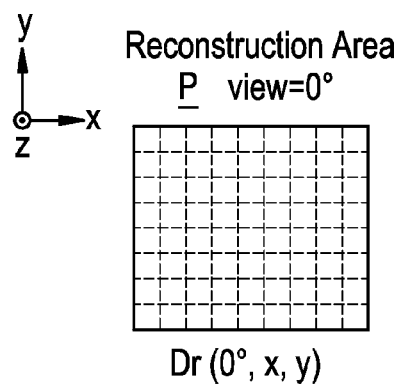
FIG. 10 is a conceptual diagram showing a state in which projection data Dr (view, x, y) are projected onto a reconstruction area.

Thus, as shown in FIG. 10, the projection data Dr (view, x, y) corresponding to the respective pixels of the reconstruction area P can be extracted.

Figure 11:
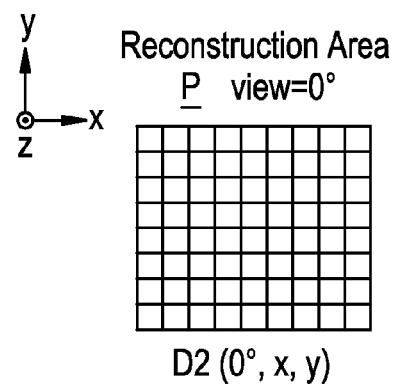
FIG. 11 is a conceptual diagram showing backprojection pixel data D2 corresponding to respective pixels on a reconstruction area.

Next, at Step S62, as shown in FIG. 7, the projection data Dr (view, x, y) are multiplied by a cone beam reconstruction weight coefficient to create projection data D2 (view, x, y) as shown in FIG. 11.

Now, the cone beam reconstruction weight function w (i, j) is as follows. Generally, when the angle which a linear line connecting the focal point of the X-ray tube 21 and a pixel g(x, y) on the reconstruction area P (xy plane) at view=βa forms with a center axis Bc of an X-ray beam is assumed to be γ and its opposite view is assumed to be view=βb in the case of fan beam image reconstruction, their relations are expressed as given by the following expression (11).

$$\beta b = \beta a + 180° - 2\gamma \quad \text{(Expression 11)}$$

When the angles which the X-ray beam passing through the pixel g(x, y) on the reconstruction area P and its opposite X-ray beam form with the reconstruction plane P, are assumed to be αa and αb respectively, they are multiplied by cone beam reconstruction weight coefficients ωa and ωb dependant on these and added together to determine backprojection pixel data D2 (0, x, y). In this case, it is given as expressed in the following expression (12).

$$D2(0,x,y) = \omega a \cdot D2(0,x,y)\_a + \omega b \cdot D2(0,x,y)\_B \quad \text{(Expression 12)}$$

where D2(0,x,y)_a shows backprojection data of view βa, and D2(0,x,y)_b shows backprojection data of view βb.

Incidentally, the sum of the cone beam reconstruction weight coefficients corresponding to the beams opposite to each other is expressed like the following expression (13):

$$\omega a + \omega b = 1 \quad \text{(Expression 13)}$$

The above addition with multiplication of the cone beam reconstruction weight coefficients ωa and ωb enables a reduction in cone angle artifact.

For example, ones determined by the following expressions can be used as the cone beam reconstruction weight coefficients ωa and ωb. Incidentally, ga indicates the weight coefficient of the view βa and gb indicates the weight coefficient of the view βb. When ½ of a fan beam angle is assumed to be γmax, the following relations are established as given by the following expressions (14) to (19):

[10]
$$ga = f(\gamma max, \alpha a, \beta a) \quad \text{(Expression 14)}$$

[11]
$$gb = f(\gamma max, \alpha b, \beta b) \quad \text{(Expression 15)}$$

[12]
$$xa = 2 \cdot ga^q / (ga^q + gb^q) \quad \text{(Expression 16)}$$

[13]
$$xb = 2 \cdot gb^q / (ga^q + gb^q) \quad \text{(Expression 17)}$$

[14]
$$wa = xa^2 \cdot (3 - 2xa) \quad \text{(Expression 18)}$$

[15]
$$wb = xb^2 \cdot (3 - 2xb) \quad \text{(Expression 19)}$$

(For example, q=1).

Assuming that max [ ] are defined as functions which adopt or take the maximum values as examples of ga and gb, for example, ga an gb are given as expressed in the following expressions (20) and (21).

[16]
$$ga = \max[0, \{(\pi/2 + \gamma max) - |\beta a|\} \cdot |\tan(\alpha a))| \quad \text{(Expression 20)}$$

[17]
$$gb = \max[0, \{(\pi/2 + \gamma max) - |\beta b|\} \cdot |\tan(\alpha b))| \quad \text{(Expression 21)}$$

In the case of the fan beam image reconstruction, each pixel on the reconstruction area P is further multiplied by a distance coefficient. Assuming that the distance from the focal point of the X-ray tube 21 to each of the detector row j and channel i of the multi-row X-ray detector 24 corresponding to the projection data Dr is r0, and the distance from the focal point of the X-ray tube 21 to each pixel on the reconstruction area P corresponding to the projection data Dr is r1, the distance coefficient is given as $(r1/r0)^2$.

In the case of parallel beam image reconstruction, each pixel on the reconstruction area P may be multiplied by the cone beam reconstruction weight coefficient w (i, j) alone.

Next, at Step S63, as shown in FIG. 7, the projection data D2 (view, x, y) is added to its corresponding backprojection data D3 (x, y) in association with each pixel.

Figure 12:
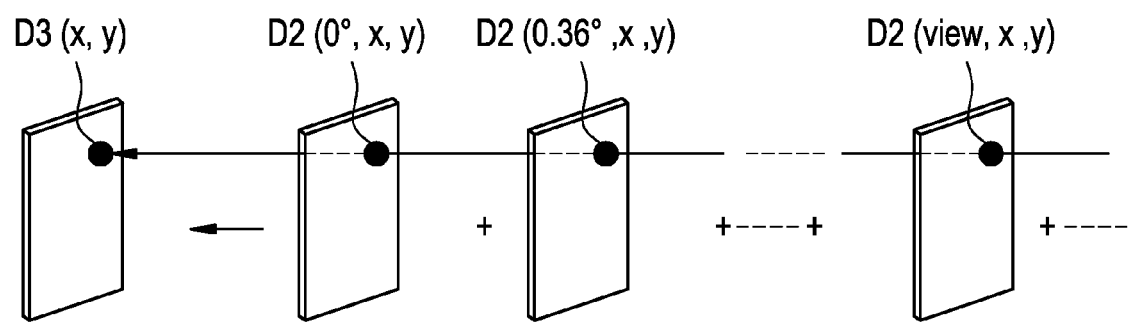
FIG. 12 is an explanatory diagram showing a state in which backprojection pixel data D2 are added together corresponding to pixels over all views to obtain backprojection data D3.

Described specifically, as shown in FIG. 12, the projection data D2 (view, x, y) is added to its corresponding backprojection data D3 (x, y) cleared in advance in association with each pixel.

Next, it is determined at Step S64 as shown in FIG. 7 whether backprojection data D2 corresponding to all views necessary for image reconstruction are added.

Here, when addition is not made (NO), Steps S61 through S63 are repeated with respect to all the views (i.e., views corresponding to 360° or views corresponding to "180°+fan angles") necessary for image reconstruction of the tomographic image to obtain backprojection data D3 (x, y) as shown in FIG. 12. On the other hand, when addition is made (Yes), the present or actual process is terminated as shown in FIG. 7.

Figure 13A:
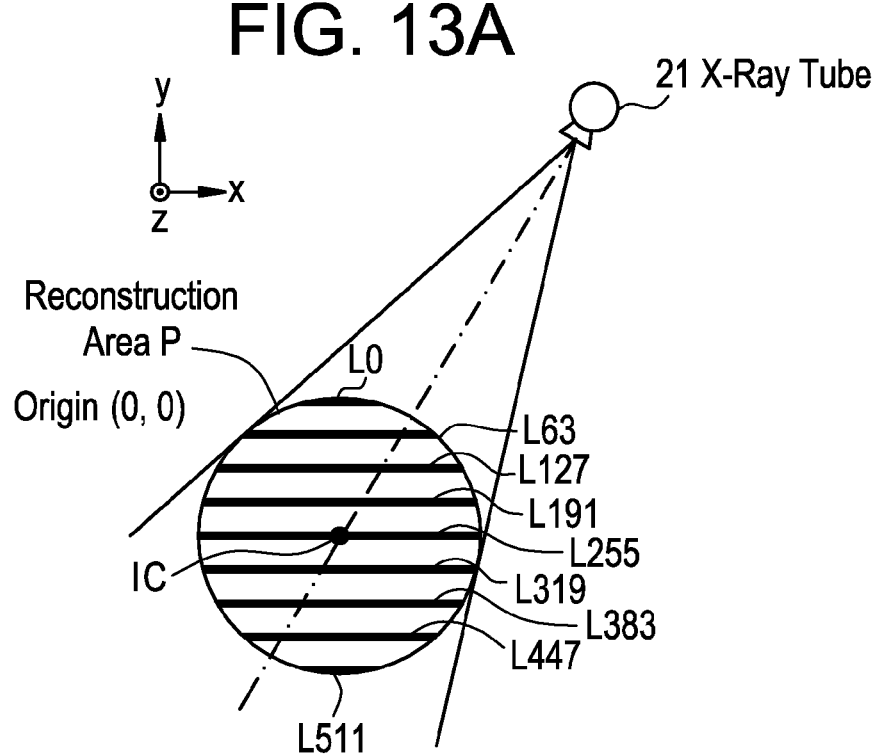
FIGS. 13a and 13b are conceptual diagrams illustrating a state in which lines on a circular reconstruction area are projected in an X-ray penetration direction.
Figure 13B:
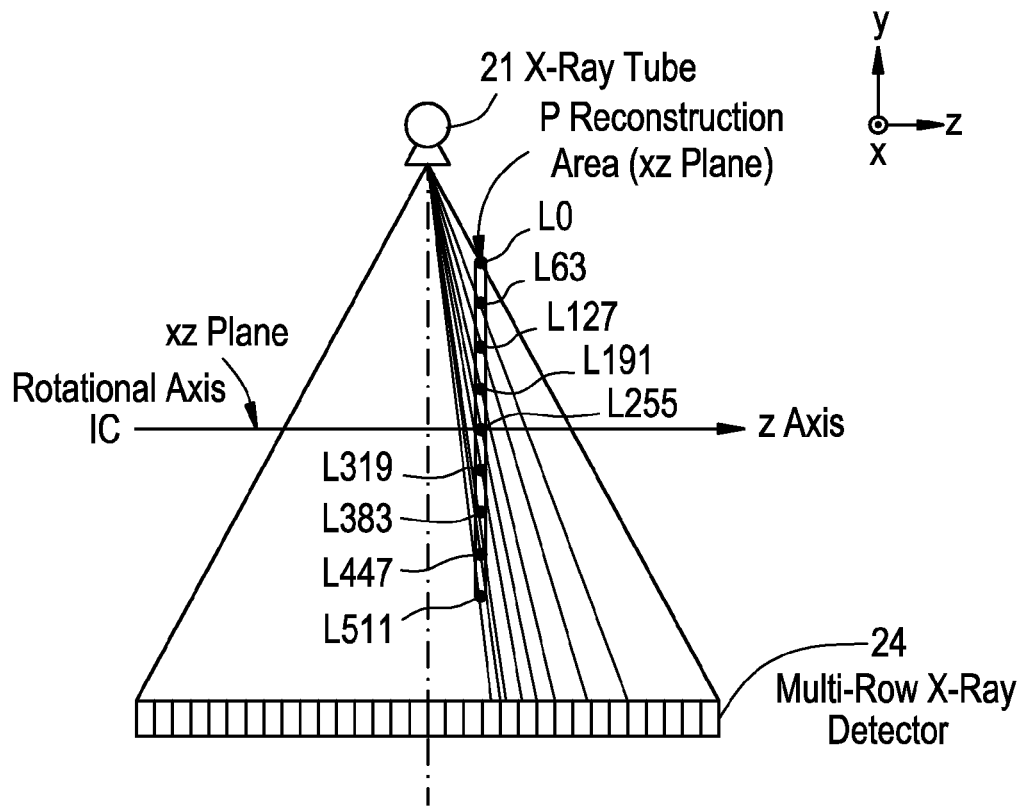

Incidentally, the reconstruction area P may be set as a circular area whose diameter is 512 pixels, without setting it as the square area of 512×512 pixels as shown in FIGS. 13(*a*) and 13(*b*).

[Operation Parameters]

Embodiments about the details of the operation parameters for the X-ray CT apparatus 100 will be explained below.

First Embodiment

The operation parameters at the helical shuttle scan are shown in the first embodiment.

Figure 18:
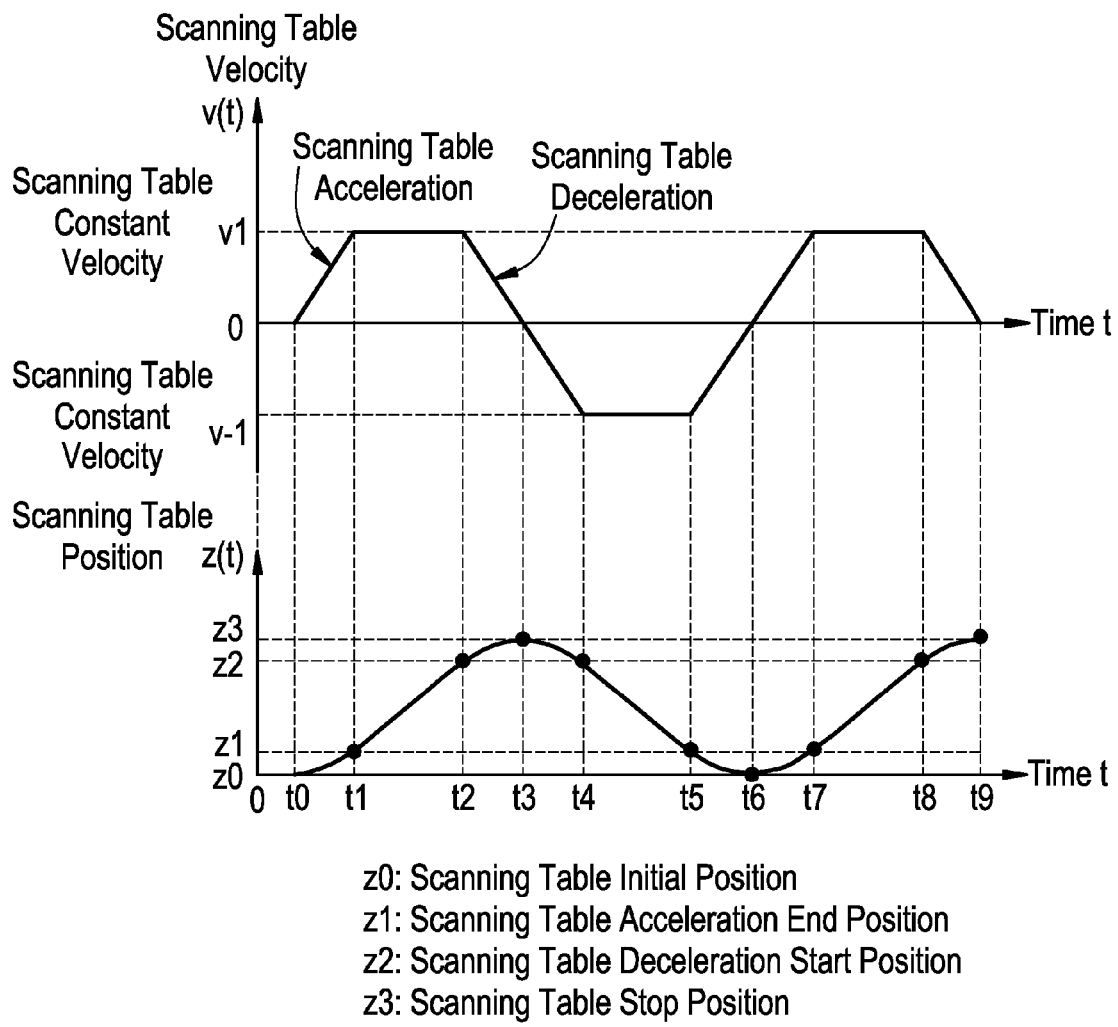
FIG. 18 is a diagram illustrating operation parameters of the scanning table (cradle) and z-direction coordinates at the helical shuttle scan.

FIG. 18 shows the z-direction operations of the scanning table at the helical shuttle scan.

In FIG. 18, z0 indicates a scanning table initial position. z1 indicates a scanning table acceleration end position. z2 indicates a scanning table deceleration start position. z3 indicates a scanning table stop position.

Here, as shown in FIG. 18, the scanning table is accelerated at a scanning table acceleration a1 in the range of z0 to z1. The scanning table is decelerated at a scanning table deceleration a2 in the range of z2 to z3. The scanning table is operated at a scanning table constant velocity v1 in the range of z1 to z2.

In the present embodiment, the scanning table is controlled using z coordinates without using the time. This is because a scanning table control device for actually controlling the scanning table is easy to control it using the z coordinates of the scanning table rather than its control using the time. Of course, the control of the scanning table is made possible similarly even where it is controlled by the time without being controlled by the z coordinates.

The helical shuttle scan is shuttled plural times as in the case of z0 to z3 to z0 to z3 as well as the above operations from z0 to z3. FIG. 18 shows the manner in which the helical shuttle scan is shuttled 1.5 times.

One example illustrative of the operation parameters for the helical shuttle scan is shown in Table of FIG. 19.

Second Embodiment

A second embodiment shows operation parameters at a variable-pitch helical scan.

Figure 20:
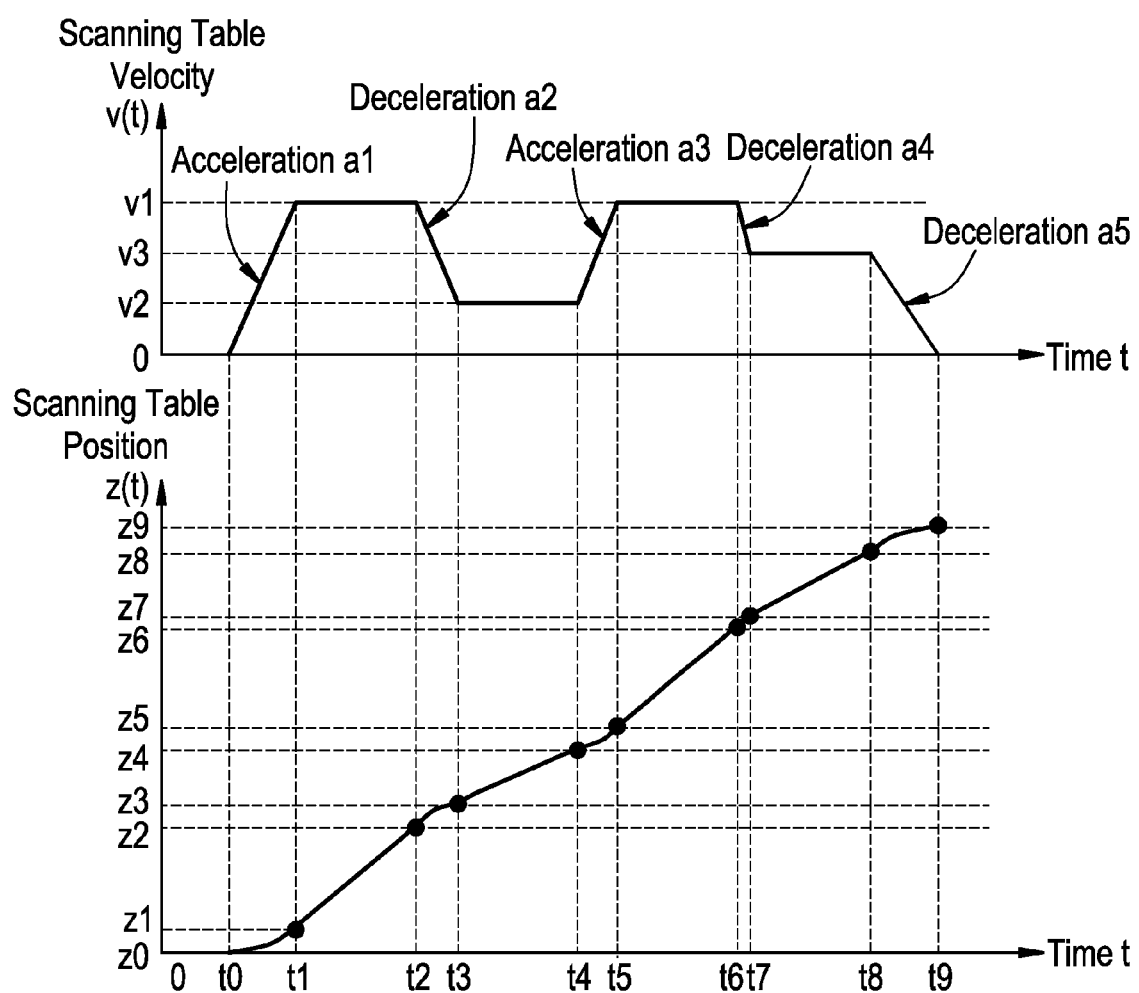
FIG. 20 is a diagram showing operation parameters of the scanning table (cradle) and z-direction coordinates at a variable-pitch helical scan.
Figure 23:
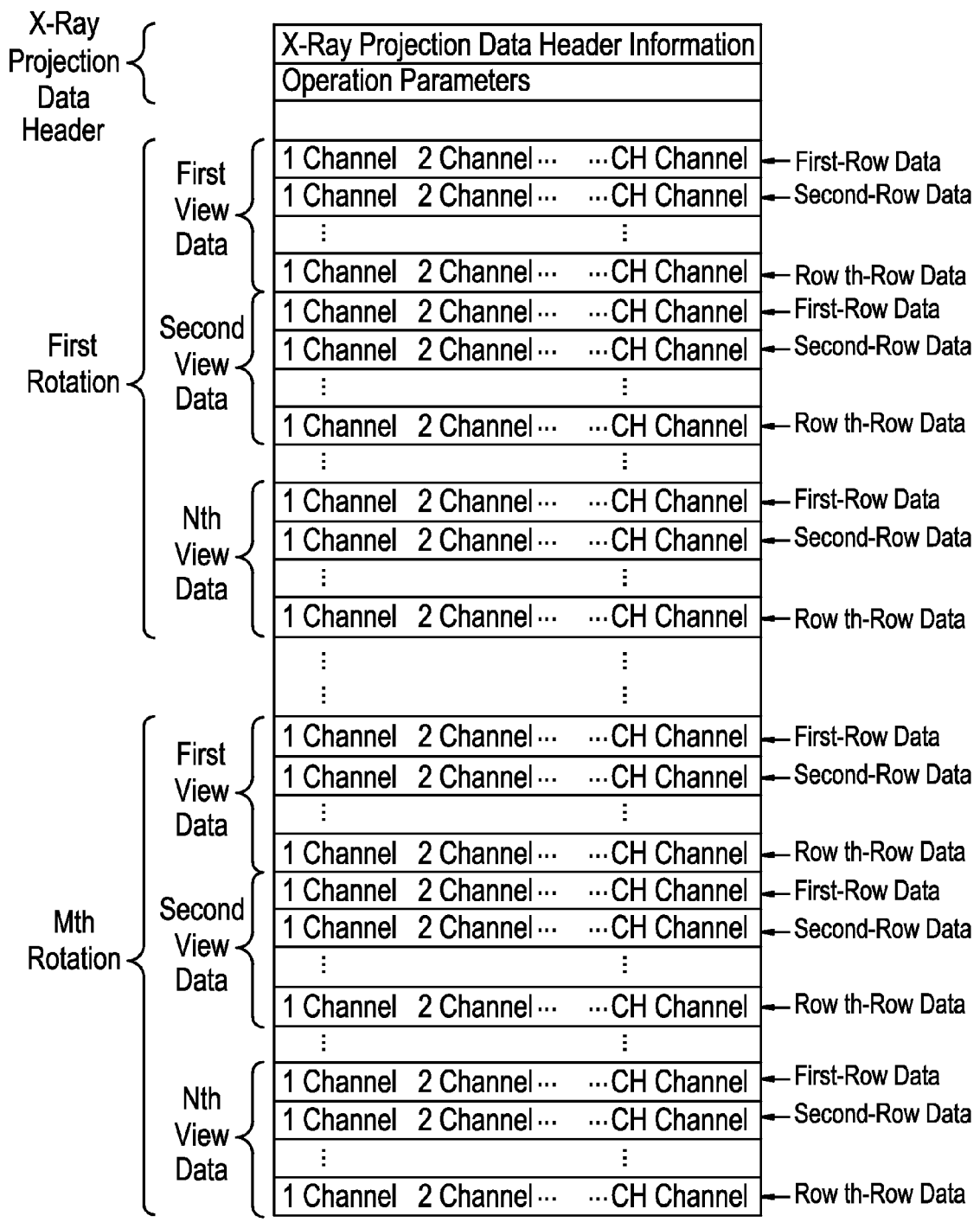
FIG. 23 is a diagram depicting a case in which operation parameters are added to X-ray projection data.

FIG. 20 shows z-direction operation parameters of the scanning table at the variable-pitch helical scan. Here, the operation parameters may be treated as another file associated with X-ray projection data or may be added to the X-ray projection data. Incidentally, FIG. 23 shows an example in which operation parameters are added to their corresponding X-ray projection data. In the X-ray projection data, an X-ray detector channel direction extends from a 1 channel to a CH channel, a row direction extends from a 1 row to a ROW row, the number of views per rotation is assumed to be N, and the number of rotations at which data acquisition is made at this time, is assumed to be M.

Operation parameters are inserted into part of header information of X-ray projection data.

In FIG. 20, z0 indicates a scanning table initial position. z1 indicates a scanning table acceleration end position. z2 indicates a scanning table deceleration start position. z3 indicates a scanning table deceleration end position. z4 indicates a scanning table acceleration start position. z5 indicates a scanning table acceleration end position. z6 indicates a scanning table deceleration start position. z7 indicates a scanning table deceleration end position. z8 indicates a scanning table deceleration start position. z9 indicates a scanning table stop position.

Here, the scanning table is accelerated at a scanning table acceleration a1 in the range of z0 to z1. The scanning table is decelerated at a scanning table deceleration a2 in the range of z2 to z3. The scanning table is accelerated at a scanning table acceleration a3 in the range of z4 to z5. The scanning table is decelerated at a scanning table deceleration a4 in the range of z6 to z7. The scanning table is decelerated at a scanning table deceleration a5 in the range of z8 to z9. The scanning table is operated at a scanning table constant velocity v1 in the range of z1 to z2. The scanning table is operated at a scanning table constant velocity v2 in the range of z3 to z4. The scanning table is operated at a scanning table constant velocity v1 in the range of z5 to z6. The scanning table is operated at a scanning table constant velocity v3 in the range of z7 to z8.

Third Embodiment

A third embodiment shows operation parameters at a scan reduced in needless exposure at the time that an X-ray data acquisition system lying in a scanning gantry is tilted during a helical scan.

Figure 21:
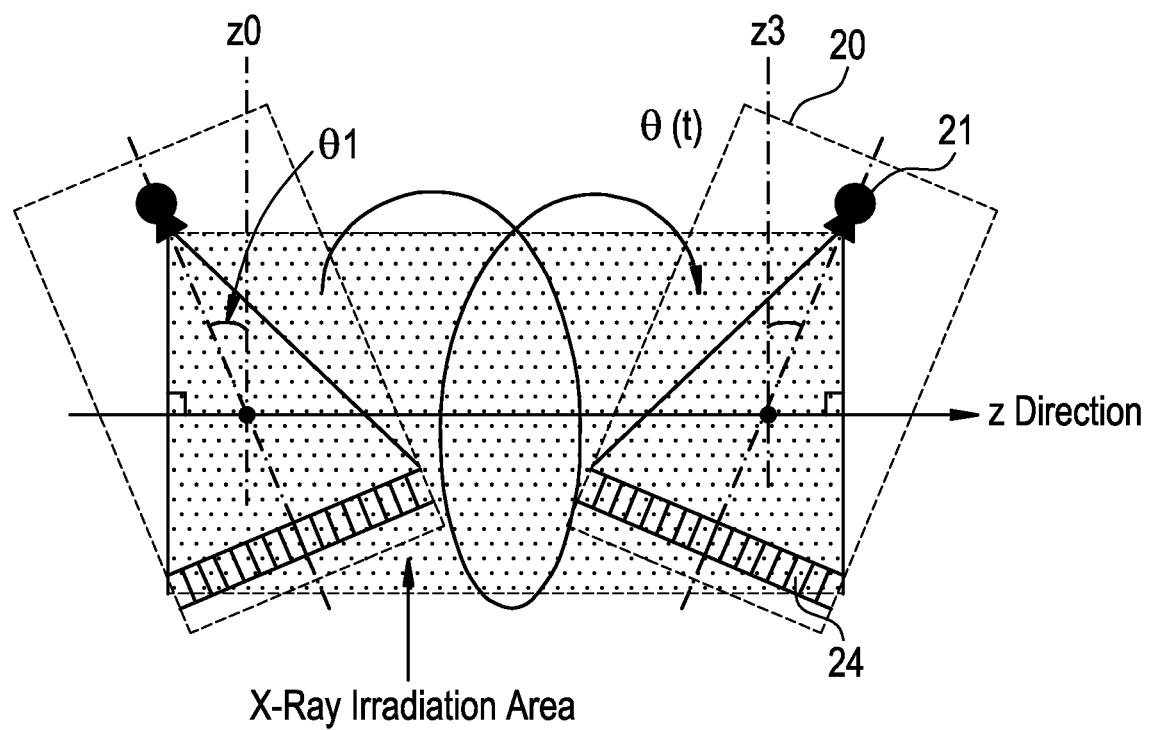
FIG. 21 is a diagram showing a scan reduced in X-ray needless exposure at the time that X-ray data acquiring device is tilted during a helical scan.

FIG. 21 shows the outline of the operation of tilting the X-ray data acquisition system in such a manner that X-ray needless exposure is reduced in the embodiment for the helical scan thereby to acquire or collect data.

Figure 22:
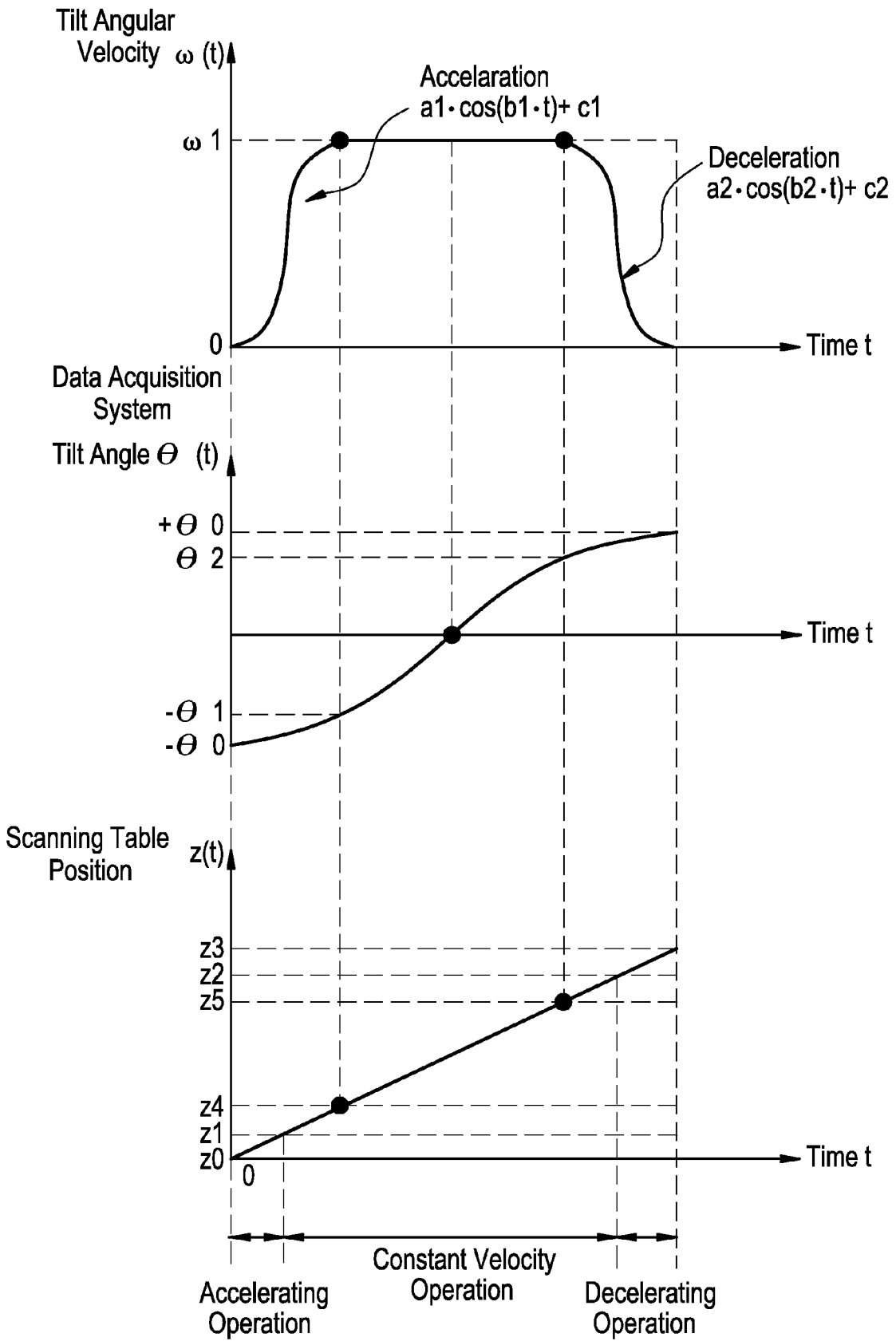
FIG. 22 is a diagram illustrating tilt operation parameters and data acquisition tilt angles of a data acquisition system at a scan reduced in X-ray needless exposure when the X-ray data acquiring device is tilted during the helical scan.

FIG. 22 shows operation parameters for tilting the X-ray data acquisition system in such a manner that the X-ray needless exposure is reduced in the embodiment for the helical scan, thereby to control tilt angles for tilting the data acquisition system upon execution of the scan.

Here, $-\theta 0$ indicates an initial value of a tilt angle of the X-ray data acquisition system. A z-direction table coordinate position at this time is z0. $-\theta 1$ indicates an acceleration end position of the tilt angle of the X-ray data acquisition system. A z-direction table coordinate position at this time is z4. $\theta 2$ indicates a deceleration start position of the tilt angle of the X-ray data acquisition system. A z-direction table coordinate position at this time is z5. $+\theta 0$ indicates a stop position of the tile angle of the X-ray data acquisition system. A z-direction table coordinate position at this time is z3. The tilt angle of the X-ray data acquisition system is accelerated in the range of $[-\theta 0, -\theta 1]$ as shown in FIG. 22.

Acceleration A at this time changes nonlinearly as expressed in the following expression (22):

[18]

$$A = a1 \cdot \cos(b1 \cdot t) + c1 \quad \text{(Expression 22)}$$

The tilt angle of the X-ray data acquisition system is decelerated in the range of $[\theta 2, +\theta 0]$.

Deceleration B at this time changes nonlinearly as expressed in the following expression (23):

[19]

$$B = a2 \cdot \cos(b2 \cdot t) + c2 \quad \text{(Expression 23)}$$

The X-ray data acquisition system is operated at a constant angular velocity $\omega 1$ in the range of $[-\theta 1, \theta 2]$.

In this case, control on the tilt of the data acquisition system is set to be carried out by a cos curve (cosine curve) in advance, whereby parameters for an accelerating operation are simplified as (a1, b1 and c1) and parameters for a decelerating operation are simplified as (a2, b2 and c2). And they can also be stored as operation parameters.

Although the operation parameters for the tilt angles of the X-ray data acquisition system have been described above, the z-direction operation parameters of the scanning table may be made similar to the first and second embodiments.

As described above, the X-ray CT apparatus 100 according to the present embodiment includes the scanning table 10 which moves the cradle 12 with the subject placed thereon within imaging space, the scanning gantry 20 which applies X rays to the subject placed on the cradle 12 moved within the imaging space and performs the scan for detecting the X-rays transmitted through the subject to thereby obtain projection data, the central processing unit 3 which controls the operations of the scanning table 10 and the scanning gantry 20 to execute the scan thereby to acquire plural projection data in time-series order and image-reconstructs by calculation, a tomographic image of the subject from the projection data obtained by execution of the scan, and the monitor 6 which displays the tomographic image image-reconstructed by the central processing unit 3 on its display screen (see FIG. 1).

Here, the scanning table 10 moves the cradle 12 along the body axial direction (z direction) of the subject placed on the cradle 12 on the basis of each control signal outputted from the central processing unit 3. The scanning gantry 20 includes the X-ray tube 21 which applies X rays from the periphery of the subject moved by the scanning table 10 to the subject within the imaging space so as to rotate with the direction extending along the z direction as the axis, and the multi-row X-ray detector 24 which detects the X rays radiated from the X-ray tube 21 and transmitted through the subject. The respective parts are controlled based on the control signals outputted from the central processing unit 3. The X-ray tube 21 applies the X rays onto the subject such that they are brought to a cone shape spread in the channel direction extending along the direction of rotation of the X-ray tube rotated around the subject and the row direction extending along the rotational-axis direction of its rotation. In the multi-row X-ray detector 24, a plurality of X-ray detectors for detecting the X rays radiated from the X-ray tube 21 and transmitted through the subject are arranged in matrix form so as to correspond to the channel and row directions (see FIGS. 2 and 3).

Upon photographing the subject by using the X-ray CT apparatus 100, the condition for performing the scan about the subject is first inputted to the input device 2 by the operator. Thereafter, the central processing unit 3 sets parameters for operating the scanning gantry 20 and parameters for moving the cradle 12 with the subject placed thereon to the scanning table 10 as viewed in the z direction, based on the condition inputted to the input device 2. For example, parameters are set such that the helical shuttle scan is carried out as described above. Described specifically, the initial position of the cradle 12 at the time that the execution of the scan is started, acceleration at which the cradle 12 is accelerated and moved from the initial position, an acceleration end position at which the acceleration and movement of the cradle is terminated, the velocity at which the cradle 12 is moved constant from the acceleration end position, a deceleration start position at which the cradle 12 moved constant is decelerated, deceleration at which the cradle 12 is decelerated and moved from the deceleration start position, a stop position where the moved cradle 12 is stopped, the timing at which projection data is obtained at the scanning gantry 2, are respectively set as parameters.

Next, the central processing unit 3 controls the operations of the scanning gantry 2 and the scanning table 10, based on the set parameters to execute a scan. For example, the helical shuttle scan is carried out based on the parameters set as described above.

At this time, the storage device 7 stores or processes a plurality of projection data obtained in a time sequence order by execution of the scan, and position data about the positions of the cradle 12 moved in the z direction when the projection data are respectively obtained, therein in association with one another upon storage of X-ray projection data or an image reconstruction process.

Here, the central processing unit 3 calculates position data about the respective positions of the cradle 12 moved in the row direction z when the projection data are respectively obtained, on the basis of both the parameters for moving the scanning gantry 20 and the parameters for moving the cradle 12 with the subject placed thereon to the scanning table 10. Thereafter, the calculated positions data and the projection data obtained by execution of the scan are respectively stored in the storage device 7 in association with one another. That is, in the present embodiment, the position data of the cradle 12 obtained by operation by device of the central processing unit 3 are stored in association with the corresponding projection data without storing the position data of the cradle 12 obtained by measurement by device of hardware such as a rotary encoder, a linear encoder or the like in association with the projection data.

Next, the central processing unit 3 image-reconstructs a tomographic image of the subject on the basis of the respective X-ray projection data and the position data stored in association with the X-ray projection data. And the monitor 6 displays the tomographic on its display screen.

Thus, in the present embodiment, the operator sets the imaging condition to thereby determine the operations of the X-ray data acquisition system and the scanning table or the cradle. That is, as the operations of the X-ray data acquisition system and the scanning table with the subject placed thereon, a scanning table z-direction coordinate position, a scanning table x-direction coordinate position, a scanning table y-direction coordinate position, a scanning gantry rotating section rotation-angle position, a scanning gantry tilt angle position, a scanning gantry x-direction coordinate position, a scanning gantry y-direction coordinate position, and a scanning gantry z-direction coordinate position are predicted upon setting of the imaging condition. Since the X-ray data acquisition system and the scanning table are normally feedback-controlled with an accuracy of 0.1 mm or less, they do not deviate vastly from their predicted values. Therefore, in the present embodiment, the operations of the X-ray data acquisition system and the scanning table can be reproduced by describing the predicted operations of the X-ray data acquisition system and the scanning table by several parameters in advance and recording the parameters.

Thus, in the present embodiment, the X-ray CT apparatus having the two-dimensional X-ray area detector of matrix structure typified by the multi-row X-ray detector or flat-panel X-ray detector is capable of efficiently storing position information and photography information of the X-ray data acquisition system at the conventional scan (axial scan), the cine scan, the helical scan, the variable-pitch helical scan or the helical shuttle scan.

Incidentally, the image reconstructing method according to the present embodiment may be a three-dimensional image reconstructing method based on a conventional known Feldkamp method. Further, another three-dimensional image reconstructing method may be adopted. Alternatively, two-dimensional image reconstruction may be used.

Although the present embodiment has described the operations in the z direction alone as the operations of the scanning table, similar effects can be brought about even in the case where the scanning table is operated in the x and y directions.

Although the present embodiment has described the tilt operations as the operations of the X-ray data acquisition system in the scanning gantry, similar effects can be brought about even in the case where the scanning gantry is operated in the x, y and z directions.

Although the first or second embodiment has described the case in which the scanning gantry 20 is not tilted, similar effects can be brought about even in the case of a so-called tilt scan in which the scanning gantry 20 is tiled.

Although the present embodiment has described the case in which the X-ray projection data acquisition is not synchronized with the biological signal, similar effects can be brought about even when synchronization with a biological signal, particularly, a cardiac signal is taken.

Although the present embodiment has described the X-ray CT apparatus having the two-dimensional X-ray area detector of the matrix structure, which is typified by the multi-row X-ray detector or the flat panel X-ray detector, similar effects can be brought about even in the case of an X-ray CT apparatus having a one-row X-ray detector.

In the present embodiment, the row-direction (z-direction) filters different in coefficient every row are convolved to adjust variations in image quality, provide a uniform slice thickness for each row, prevent the occurrence of artifacts and realize the quality of an image low in noise. Although various z-direction filter coefficients are considered therefor, any can bring about similar effects.

Although the present embodiment has been described on the basis of the medical X-ray CT apparatus, it can be applied even to an X-ray CT-PET apparatus, an X-ray CT-SPEC apparatus and the like combined with an industrial X-ray CT apparatus or other apparatus.

The invention claimed is:

1. An X-ray CT apparatus comprising:
    a scanning table configured to support a subject thereon and to move the subject within the X-ray CT apparatus;
    a scanning gantry comprising:
        an X-ray generator;
        an X-ray detector configured to detect X-rays generated by the X-ray generator, the X-ray detector positioned in opposition to the X-ray generator; and
        a rotation device configured to rotate the X-ray generator and the X-ray detector, the X-ray generator configured to expose the X-rays to the subject moved by the scanning table while the X-ray generator and the X-ray detector are rotated about the subject, the scanning gantry configured to perform a scan including detecting the X-rays transmitted through the subject at the X-ray detector to acquire X-ray projection data;
    a scanning condition setting device configured to set parameters for controlling a movement of the scanning table along a moving direction during the scan, the parameters including an acceleration and a deceleration of the movement of the scanning table;
    a predicting device configured to predict a plurality of positions of the scanning table along the moving direction for each view of the scan by calculating the plurality of positions of the scanning table using the parameters set by the scanning condition setting device; and
    an image reconstructing device configured to reconstruct a plurality of tomographic images within a range scanned during the acceleration and the deceleration of the movement of the scanning table along the moving direction by reconstructing the X-ray projection data, wherein the X-ray projection data is correlated to the plurality of predicted positions.

2. The X-ray CT apparatus according to claim 1, wherein the parameters comprise at least one of a scanning table acceleration, a scanning table deceleration, a scanning table constant velocity, a scanning table initial position, a scanning table stop position, a scanning table acceleration end position, and a scanning table deceleration start position.

3. The X-ray CT apparatus according to claim 1, wherein the predicting device is further configured to add the parameters to the X-ray projection data as a part of header information of the X-ray projection data.

4. The X-ray CT apparatus according to claim 1, wherein the predicting device is further configured to record the parameters to a file associated with the X-ray projection data.

5. The X-ray CT apparatus according to claim 1, wherein the scanning condition setting device is further configured to set as one of the parameters a tilt parameter for controlling a tilt angle of the scanning gantry during the scan, and wherein the predicting device is configured to calculate the plurality of positions by using the parameters and the tilt parameter.

6. The X-ray CT apparatus according to claim 1, wherein the scan is a helical shuttle scan.

7. The X-ray CT apparatus according to claim 1, wherein the image reconstructing device is configured to perform a three-dimensional image reconstruction.

8. A method for producing an X-ray CT image by reconstructing projection data, said method comprising:

obtaining the projection data during a scan including an acceleration and a deceleration of a movement of a scanning table using an X-ray CT apparatus, wherein the X-ray CT apparatus comprises the scanning table configured to support a subject thereon and to move the subject within the X-ray CT apparatus, and a scanning gantry comprising an X-ray generator, an X-ray detector configured to detect X-rays generated by the X-ray generator, the X-ray detector positioned in opposition to the X-ray generator, and a rotation device configured to rotate the X-ray generator and the X-ray detector, the X-ray generator configured to expose the X-rays to the subject moved by the scanning table while the X-ray generator and the X-ray detector are rotated about the subject, the scanning gantry configured to perform the scan including detecting the X-rays transmitted through the subject at the X-ray detector to acquire the projection data;

predicting a plurality of positions of the scanning table along a moving direction for each view of the scan by calculating the plurality of positions of the scanning table using parameters for controlling movement of the scanning table along the moving direction; and reconstructing a plurality of tomographic images within a range scanned during the acceleration and the deceleration of the movement of the scanning table by reconstructing the projection data, wherein the projection data are correlated to the plurality of predicted positions.

9. The method for producing X-ray CT image according to claim 8, wherein predicting a plurality of positions further comprises calculating the plurality of positions of the scanning table using parameters comprising at least one of a scanning table acceleration, a scanning table deceleration, a scanning table constant velocity, a scanning table initial position, a scanning table stop position, a scanning table acceleration end position, and a scanning table deceleration start position.

10. The method for producing X-ray CT image according to claim 8 further comprising adding the parameters to the projection data as a part of header information of the projection data.

11. The method for producing X-ray CT image according to claim 8 further comprising recording the parameters to a file associated with the projection data.

12. The method for producing X-ray CT image according to claim 8, wherein predicting a plurality of positions of the scanning table further comprises using the parameters and a tilt parameter for controlling a tilt angle of the scanning gantry during, the scan to predict the plurality of positions.

13. The method for producing X-ray CT image according to claim 8, wherein obtaining the projection data during a scan further comprises performing a helical shuttle scan.

14. The method for producing X-ray CT image according to claim 8, wherein reconstructing a plurality of tomographic images further comprises performing a three-dimensional image reconstruction.

* * * * *